(12) United States Patent
Brahmbhatt et al.

(10) Patent No.: US 10,426,736 B2
(45) Date of Patent: *Oct. 1, 2019

(54) DELIVERING FUNCTIONAL NUCLEIC ACIDS TO MAMMALIAN CELLS VIA BACTERIALLY-DERIVED, INTACT MINICELLS

(71) Applicant: EnGeneIC Molecular Delivery Pty. Ltd., Sydney (AU)

(72) Inventors: Himanshu Brahmbhatt, Sydney (AU); Jennifer MacDiarmid, Sydney (AU)

(73) Assignee: ENGENEIC MOLECULAR DELIVERY PTY. LTD., Sydney (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,548

(22) Filed: Aug. 11, 2017

(65) Prior Publication Data

US 2018/0028456 A1    Feb. 1, 2018

Related U.S. Application Data

(60) Continuation of application No. 14/983,126, filed on Dec. 29, 2015, now Pat. No. 9,730,897, which is a division of application No. 14/152,979, filed on Jan. 10, 2014, now Pat. No. 9,242,007, which is a division of application No. 11/211,098, filed on Aug. 25, 2005, now Pat. No. 8,691,963.

(60) Provisional application No. 60/604,433, filed on Aug. 26, 2004.

(51) Int. Cl.

| | | |
|---|---|---|
| A61K 48/00 | (2006.01) | |
| C07H 21/02 | (2006.01) | |
| C07H 21/04 | (2006.01) | |
| C12N 15/113 | (2010.01) | |
| A61K 9/50 | (2006.01) | |
| C07K 16/12 | (2006.01) | |
| C07K 16/28 | (2006.01) | |
| C12N 15/11 | (2006.01) | |
| A61K 31/713 | (2006.01) | |
| A61K 47/46 | (2006.01) | |
| A61K 39/40 | (2006.01) | |
| C07K 16/40 | (2006.01) | |
| A61K 31/4745 | (2006.01) | |
| A61K 39/395 | (2006.01) | |
| A61K 47/69 | (2017.01) | |

(52) U.S. Cl.
CPC ........ *A61K 9/5068* (2013.01); *A61K 31/4745* (2013.01); *A61K 31/713* (2013.01); *A61K 39/39558* (2013.01); *A61K 39/40* (2013.01); *A61K 47/46* (2013.01); *A61K 47/6901* (2017.08); *A61K 47/6923* (2017.08); *A61K 48/0008* (2013.01); *C07K 16/1235* (2013.01); *C07K 16/2863* (2013.01); *C07K 16/40* (2013.01); *C12N 15/111* (2013.01); *C12N 15/113* (2013.01); *C12N 15/1135* (2013.01); *C12N 15/1137* (2013.01); *C12N 15/1138* (2013.01); *C07K 2317/31* (2013.01); *C12N 2310/11* (2013.01); *C12N 2310/111* (2013.01); *C12N 2310/14* (2013.01); *C12N 2310/141* (2013.01); *C12N 2310/531* (2013.01); *C12N 2320/32* (2013.01); *Y02A 50/473* (2018.01)

(58) Field of Classification Search
CPC .......................... C12N 15/113; C12N 2310/11
See application file for complete search history.

(56) References Cited

U.S. PATENT DOCUMENTS

| | | |
|---|---|---|
| 3,817,837 A | 6/1974 | Rubenstein |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,496,778 A | 1/1985 | Myers et al. |
| 4,975,278 A | 12/1990 | Senter et al. |
| 4,987,071 A | 1/1991 | Cech et al. |
| 5,037,743 A | 8/1991 | Welch et al. |
| 5,143,830 A | 9/1992 | Holland et al. |
| 5,260,203 A | 11/1993 | Ladner et al. |
| 5,455,030 A | 10/1995 | Ladner et al. |
| 5,530,101 A | 6/1996 | Queen et al. |
| 5,585,089 A | 12/1996 | Queen et al. |
| 6,025,197 A | 2/2000 | Sheppard |
| 6,635,448 B2 | 10/2003 | Bucciarelli et al. |

(Continued)

FOREIGN PATENT DOCUMENTS

| | | |
|---|---|---|
| CN | 101715489 A | 5/2016 |
| JP | 10-075793 | 3/1998 |

(Continued)

OTHER PUBLICATIONS

Notice of Allowance issued in co-pending U.S. Appl. No. 14/744,848, dated Jun. 8, 2018.

(Continued)

*Primary Examiner* — Amy H Bowman
(74) *Attorney, Agent, or Firm* — Foley & Lardner LLP

(57) ABSTRACT

Intact bacterially derived minicells containing functional nucleic acids or plasmids encoding functional nucleic acids can reduce, in targeted mammalian cells, drug resistance, apoptosis resistance, and neoplasticity, respectively. Methodology that employs minicells to deliver functional nucleic acids, targeting the transcripts of proteins that contribute to drug resistance or apoptosis resistance, inter alia, can be combined with chemotherapy to increase the effectiveness of the chemotherapy.

19 Claims, 6 Drawing Sheets

Specification includes a Sequence Listing.

(56) References Cited

U.S. PATENT DOCUMENTS

| | | | |
|---|---|---|---|
| 6,639,055 | B1 | 10/2003 | Carter et al. |
| 7,011,946 | B2 | 3/2006 | Raychaudhuri et al. |
| 7,125,679 | B2 | 10/2006 | Ashkar |
| 7,183,105 | B2 | 2/2007 | Sabbadini et al. |
| 2002/0068709 | A1 | 6/2002 | Orum et al. |
| 2003/0203481 | A1 | 10/2003 | Surber et al. |
| 2004/0180844 | A1 | 9/2004 | Fesik |
| 2004/0265994 | A1 | 12/2004 | Brahmbhatt et al. |
| 2007/0166446 | A1 | 7/2007 | Boursier |
| 2007/0237744 | A1 | 10/2007 | Brahmbhatt et al. |
| 2007/0241067 | A1 | 10/2007 | Brahmbhatt et al. |
| 2007/0298056 | A1 | 12/2007 | Brahmbhatt et al. |
| 2008/0038296 | A1 | 2/2008 | Brahmbhatt et al. |
| 2008/0051469 | A1 | 2/2008 | Brahmbhatt et al. |
| 2008/0299084 | A1 | 12/2008 | Brahmbhatt et al. |

FOREIGN PATENT DOCUMENTS

| | | |
|---|---|---|
| JP | 10-502819 | 3/1998 |
| WO | WO-81/01145 | 4/1981 |
| WO | WO-88/07378 | 10/1988 |
| WO | WO 95/21191 | 8/1995 |
| WO | WO-96/02556 | 2/1996 |
| WO | WO-00/63364 A2 | 10/2000 |
| WO | WO-00/67776 | 11/2000 |
| WO | WO-02/17852 A2 | 3/2002 |
| WO | WO-03/033519 A2 | 4/2003 |
| WO | WO 03/072014 A2 | 9/2003 |
| WO | WO-2004/022771 A | 3/2004 |
| WO | WO-2005/056749 A2 | 6/2005 |
| WO | WO-2005/079584 A2 | 9/2005 |
| WO | WO-2005/079854 A1 | 9/2005 |
| WO | WO-2006/021894 A | 3/2006 |
| WO | WO-2006/066048 A2 | 6/2006 |
| WO | WO 2009/027830 A1 | 3/2009 |

OTHER PUBLICATIONS

Office Action issued in related U.S. Appl. No. 14/744,848, dated Jul. 24, 2017.
Aagaard, et al., "RNAi therapeutics: Principles, prospects and challenges." Advanced Drug Delivery Reviews 59. 2007. pp. 75-86.
Achim Knappik et al., "Fully Synthetic Human Combinatorial Antibody Libraries (HuCAL) Based on Modular Consensus Frameworks and CDRs Randomized with Trinucleotides", J. Mol. Biol., 2000, vol. 296, pp. 57-86.
Advisory Action dated Jun. 24, 2010 for U.S. Appl. No. 10/978,680 (3 pages).
Ae Frankel et al., "Diphtheria toxin fused to human interleukin-3 is toxic to blasts from patients with myeloid leukemias", Leukemia, 2000, vol. 14, pp. 576-585.
Ajay Bakhshi et al., "Cloning the chromosomal Breakpoint of t(14;18) Human Lymphomas: Clustering around JH on Chromosome 14 and near a Transcriptional Unit on 18", Cell, 1985, vol. 41, pp. 899-906.
Alan Bridge et al., "Induction of an interferon response by RNAi vectors in mammalian cells," Nature Genetics, vol. 34, No. 3, (2003), pp. 263-264.
Alan F. List, MD et al., "Phase I/II Trial of Cyclosporine as a Chemotherapy-Resistance Modifier in Acute Leukemia", Journal of Clinical Oncology, 1993, vol. 11, No. 9, pp. 1652-1660.
Alan F. List, MD, "Multidrug Resistance: Clinical Relevance in Acute Leukemia", Oncology, 1993, vol. 7, No. 10, pp. 23-38.
Aline Jaffe et al., "Minicell-Forming Mutants of *Escherichia coli*: Production of Minicells and Anucleate Rods", Journal of Bacteriology, vol. 170, No. 7, Jul. 1988, pp. 3094-3101.
Alla Grishok et al., "Genetic Requirements for Inheritance of RNAi in C. elegans", Science, vol. 287, Mar. 31, 2000, pp. 2494-2497.
Andrew D. Griffiths et al., "Isolation of high affinity human antibodies directly from large synthetic repertoires", The EMBO Journal, 1994, vol. 13, No. 14, pp. 3245-3260.

Aneta Todorovska et al., "Design and application of diabodies, triabodies and tetrabodies for cancer targeting", Journal of Immunological Methods 248(2001) 47-66.
Ann H. Cory et al., "Use of an Aqueous Soluble Tetrazolium/Formazan Assay for Cell Growth Assays in Culture", Cancer Communications vol. 3, No. 7, 1991, pp. 207-212.
Anne Blangy et al., "Phosphorylation by p34cdc2 Regulates Spindle Association of Human Eg5, a Kinesin-Related Motor Essential for Bipolar Spindle Formation in Vivo", Cell, vol. 83, pp. 1159-1169, Dec. 29, 1995.
Anne T. Perrotta et al., "Cleavage of Oligoribonucleotides by a Ribozyme Derived from the Hepatitis ∂ Virus RNA Sequence", Biochemistry 1992, 31, pp. 16-21.
Annmarie Palione et al., "Mutation of a Gene That Encodes a Kinesin-like Protein Blocks Nuclear Division in A. nidulans", Cell, vol. 60, 1019-1027, Mar. 23, 1990.
Anthony J. Mason et al., "The Hypogonadal Mouse : Reproductive Functions Restored by Gene Therapy", Science, 1986, vol. 234, pp. 1372-1378.
Arnold Hampel et al., "'Hairpin' catalytic RNA model: evidence for helices and sequence requirement for substrate RNA", Nucleic Acids Research, 1990, vol. 18, No. 2, pp. 299-304.
Arnold Hampel et al., "RNA Catalytic Properties of the Minimum (-)sTRSV Sequence", Biochemistry, 1989, vol. 28, No. 12, pp. 4929-4933.
Assem-Galal Ziady et al., "Gene transfer into hepatoma cell lines via the serpin enzyme complex receptor", Am. J. Physiol. 273: G545-G552 (1997).
Aya Leder et al., "Consequences of Widespread Deregulation of the c-myc Gene in Transgenic Mice: Multiple Neoplasms and Normal Development", Cell, 1986, vol. 45, pp. 485-495.
B.L. Geller et al., "Antisense Phosphorodiamidate Morpholino Oligomer Inhibits Viability of *Escherichia coli* in Pure Culture and in Mouse Peritonitis", Journal of Antimicrobial Chemotherapy, Oxford University Press, GB, vol. 55, May 4, 2005, pp. 983-988, XP003008448.
Barbara C.M. Van De Weerdt et al., "Polo-Like Kinases A Team in Control of the Division", Cell Cycle 5:8, 853-864, Apr. 15, 2006.
Barry J. Saville et al., "A Site-Specific Self-Cleavage Reaction Performed by a Novel RNA in Neurospora Mitochondria", Cell, vol. 61, 685-696, May 18, 1990.
Barry J. Saville et al., "RNA-mediated ligation of self-cleavage products of a Neurospora mitochondrial plasmid transcript", Proc. Natl. Acad. Sci. USA, vol. 88, pp. 8826-8830, Oct. 1991.
Bates et al., "Dynamics of DNA Molecules in a Membrane Channel Probed by Active Control Techniques." Biophysical Journal. 2003. vol. 84. pp. 2366-2372.
Bertrand et al., Comparison of Antisense Oligonucleotides and siRNAs in Cell Culture and in Vivo, *Biochemical and Biophysical Research Communications*, vol. 296, pp. 1000-1004 (2002).
Biroccio, et al., The future of antisense therapy: combination with anticancer treatments, Oncogene, vol. 22, pp. 6579-6588.
Boris Karpovsky et al., "Production of Target-Specific Effector Cells Using Hetero-Cross-Linked Aggregates Containing Anti-Target Cell and Anti-Fc( Receptor Antibodies", Journal of Experimental Medicine, 1984, vol. 160, pp. 1686-1701.
Brett P. Monia et al., "Nuclease Resistance and Antisense Activity of Modified Oligonucleotides Targeted to Ha-ras", The Journal of Biological Chemistry, vol. 271, No. 24, Issue of Jun. 14, 1996, pp. 14533-14540.
Bridge et al., Induction of an Interferon Response by RNAi Vectors in Mammalian Cells, *Nature Genetics*, vol. 34, No. 3, pp. 263-264 (2003).
C. S. Kaetzel et al., "The polymeric immunoglobulin receptor: structure and synthesis", Biochemical Society Transactions, 1997, vol. 25, No. 2, pp. 475-480.
Canadian Examination Report from corresponding Canadian Application No. 2,682,704 dated Jun. 6, 2012.
Canadian Office Action Application No. 2 577 938 dated Jul. 28, 2010.

(56) References Cited

OTHER PUBLICATIONS

Carl A. Pinkert et al., "An albumin enhancer located 10 kb upstream functions along with its promoter to direct efficient, liver-specific expression in transgenic mice", Genes & Development 1:268-276, 1987.
Carl. A. Doige et al., "ATP-Dependent Transport Systems in Bacteria and Humans: Relevance to Cystic Fibrosis and Multidrug Resistance", Annu. Rev. Microbiol. 1993, 47:290-319.
Carol Readhead et al., "Expression of a Myelin Basic Protein Gene in Transgenic Shiverer Mice: Correction of the Dysmyelinating Phenotype", Cell, vol. 48, Feb. 27, 1987, pp. 703-712.
Catherine Grillot-Courvalin et al., "Wild-type intracellular bacteria delivery DNA into mammalian cells," Cellular Microbiology, vol. 4, No. 3, (2002), pp. 177-186.
Cecilia Guerrier-Takada et al., "The RNA Moiety of Ribonuclease P is the Catalytic Subunit of the Enzyme", Cell, vol. 35, 849-857, Dec. 1983 (Part 2).
Christelle Souriau et al., "Recombinant antibodies for cancer diagnosis and therapy", Expert Opin. Biol. Ther., 2001, vol. 1, No. 5, pp. 845-855.
Christian M. Becker et al., "Gene Therapy of Prostate Cancer with the Soluble Vascular Endothelial Growth Factor Receptor Flk1", Cancer Biology & Therapy, 1:5, 548-553, Sep./Oct. 2002.
Christiane Nieth et al., "Modulation of the classical multidrug resistance (MDR) phenotype by RNA interference (RNAi)", FEBS Letters 545 (2003) pp. 144-150.
Christoph Mamot et al., "Epidermal Growth Factor Receptor (EGFR)-targeted Immunoliposomes Mediate Specific and Efficient Drug Delivery to EGFR- and EGFRvlll-overexpressing Tumor Cells", Cancer Research, Jun. 2003, vol. 63, 3154-3161.
Christopher F. Higgins, "ABC transporters: physiology, structure and mechanism—an overview", Res. Microbiol. 152 (2001) 205-210.
Christopher L. Morton et al., "Rhabdomyosarcoma-Specific Expression of the Herpes Simplex Virus Thymidine Kinase Gene Confers Sensitivity to Ganciclovir", The Journal of Pharmacology & Experimental Therapeutics, vol. 286, No. 2, 1998, pp. 1066-1073.
Communication pursuant to Article 94(3) EPC EP Application No. 05 806 875.0 dated Dec. 30, 2010.
Cun-Yu Wang et al., "Control of inducible chemoresistance: Enhanced anti-tumor therapy through increased apoptosis by inhibition of NF-κB", Nature Medicine, vol. 5, No. 4, Apr. 1999, pp. 412-417.
David M. Glover et al., "Polo-like kinases: a team that plays throughout mitosis", Genes & Development 12:3775-3787.
David M. Raskin et al., "MinDE-Dependent Pole-to-Pole Oscillation of Division Inhibitor MinC in *Escherichia coli*", Journal of Bacteriology, vol. 181, No. 20, Oct. 1999, pp. 6419-6424.
David P. Speert et al., "Functional Characterization of Macrophage Receptors for In Vitro Phagocytosis of Unopsonized Pseudomonas aeruginosa", J. Clin. Invest. vol. 82, Sep. 1988, pp. 872-879.
David S. Salomon et al., "Epidermal growth factor-related peptides and their receptors in human malignancies", Critical Reviews in Oncology/Hematogology, 19 (1995) pp. 183-232.
David V. Morrissey et al., "Activity of Stabilized Sort Interfering RNA in a Mouse Model of Hepatitis B Virus Replication", Hepatology 2005; 41:1349-1356.
Dawn E. Colwell et al., "Monoclonal Antibodies to *Salmonella lipopolysaccharide*: Anti-O-Polysaccharide Antibodies Protect C3H Mice Against Challenge with Virulent *Salmonella typhimurium*," The Journal of Immunology, vol. 133, No. 2, Aug. 1984, pp. 950-957.
Decad & Nikaido (1976) "Outer Membrane of Gram-Negative Bacteria: XII. Molecular-Sieving Function of Cell Wall" Journal of Bacteriology 128(1):325-336.
Delcour, Anne H., "Outer membrane permeability and antibiotic resistance." Biochemica et Biophysica Acta 1794. 2009. pp. 806-816.
Denise R. Shaw et al., "Phagocytosis requires repeated triggering of macrophage phagocytic receptors during particle ingestion", Nature, vol. 289, Jan. 29, 1981, pp. 409-411.

Derek M. Dykxhoorn et al., "The Silent Revolution: RNA Interference as Basic Biology, Research Tool and Therapeutic", Annu. Rev. Med. 2005, 56:401-423.
Dm Dykxhoorn et al., "The silent treatment: siRNAs as small molecule drugs", Gene Therapy (2006) 13, 541-552.
Dong Xu et al., "Strategies for Inhibition of MDR1 Gene Expression", Molecular Pharmacology, Aug. 1, 2004, pp. 268-275, vol. 66, No. 2.
Dong Xu et al., "Strategies for Inhibition of MDR1 Gene Expression", Molecular Pharmacology, vol. 66, No. 2, pp. 268-275, 2004.
Douglas C. Prasher "Using GFP to see the light", TIG, vol. 11, No. 8, Aug. 1995, pp. 320-323.
Douglas Hanahan, "Heritable formation of pancreatic (-cell tumours in transgenic mice expressing recombinant insulin/simian virus 40 oncogenes", Nature, 1985, vol. 315, pp. 115-122.
E Yagüe et al., "Complete reversal of multidrug resistance by stable expression of small interfering RNAs targeting MDR1", Gene Therapy 2004, 11, 1170-1174.
E.J. Harry, "Bacterial cell division: regulating Z-ring formation", Molecular Microbiology, 2001, vol. 40, No. 4, pp. 795-803.
E.M. Dagenbach et al., "Erratum—A new kinesin tree", J. Cell Sci. 117, 3-7.
Emmanouil D. Karagiannis et al., "Minicells overcome tumor drug-resistance", Nature Biotechnology, vol. 27, No. 7, Jul. 2009, pp. 620-621.
Eric Devroe et al., "Therapeutic potential of retroviral RNAi vectors", Expert Opin. Biol. Ther. (2004) 4(3):319-327.
Erika Check, "Gene therapy put on hold as third child develops cancer", Nature, vol. 433, Feb. 10, 2005, p. 561.
European Search Report for application No. EP 05806875.0, dated Feb. 12, 2009.
European Search Report from corresponding EP Application No. 11171410, dated May 30, 2012.
Final Office Action U.S. Appl. No. 11/211,098 dated May 13, 2011.
Final Office Action U.S. Appl. No. 12/053,197 dated Mar. 10, 2010.
Francis A. Barr et al., "Polo-Like Kinases and the Orchestration of Cell Division", Nature Reviews/Molecular Cell Biology vol. 5, Jun. 2004, pp. 429-440.
Françoise Van Bambeke et al., "Antibiotic Efflux Pumps", Biochemical Pharmacology, vol. 60, pp. 457-470, 2000.
Frank Czauderna et al., "Structural variations and stabilizing modifications of synthetic siRNAs in mammalian cells", Nucleic Acids Research vol. 31, No. 11, 2003, pp. 2705-2716.
G. Harth et al., "Treatment of Mycobacterium tuberculosis with antisense oligonucleotides to glutamine synthetase mRNA inhibits glutamine synthetase activity, formation of the poly-L-glutamate/glutamine cell wall structure, and bacterial replication", Proceedings of the National Academy of Sciences of the United States of America, Jan. 2000, vol. 97, No. 1, pp. 418-423, XP002518881.
Galvin H. Swift et al., "Tissue-Specific Expression of the Rat Pancreatic Elastase I Gene in Transgenic Mice", Cell, vol. 38, 639-646, Oct. 1984.
Gary D. Kruh et al., "The MRP family of drug efflux pumps", Oncogene (2003) 22, pp. 7537-7552.
Gary J. Doherty et al., "Mechanisms and Endocytosis", Annu. Rev. Biochem. Mar. 14, 2009,78:31.1-31.46.
Gavin D. Kelsey et al., "Species- and tissue-specific expression of human α1-antitrypsin in transgenic mice", Genes & Development, 1987, vol. 1, pp. 161-171.
Gennaro Ciliberto et al., "Cell-Specific Expression of a Transfected Human α1-Antitrypsin Gene", Cell, 1985, vol. 41, pp. 531-540.
George L. Sheffer MS et al., "Lung resistance related protein/major vault protein and vaults in multidrug-resistance cancer", Current Opinion in Oncology, 2000, 12 :550-556.
Gregory J. Hannon, "RNA interference", Nature, 2002, vol. 418, pp. 244-251.
Guy S. Salvesen et al., "Caspases: Intracellular Signaling by Proteolysis", Cell, vol. 91, 443-446, Nov. 14, 1997.
György Hutvágner et al., "RNAi: nature abhors a double-strand", Current Opinion in Genetics & Development, 2002, 12 :225-232.
H. Brahmbhatt et al., U.S. PTO Notice of Allowance, U.S. Appl. No. 10/602,021 dated Jun. 22, 2009, 5 pgs.

(56) References Cited

OTHER PUBLICATIONS

H. Brahmbhatt et al., U.S. PTO Office Action, U.S. Appl. No. 10/581,990 dated Mar. 19, 2009, 32 pgs.
H. Brahmbhatt et al., U.S. PTO Office Action, U.S. Appl. No. 10/588,028 dated Mar. 18, 2009, 22 pgs.
H. Brahmbhatt et al., U.S. PTO Office Action, U.S. Appl. No. 10/602,021 dated May 4, 2006, 10 pgs.
H. Brahmbhatt et al., U.S. PTO Office Action, U.S. Appl. No. 10/602,021 dated May 15, 2007, 10 pgs.
H. Brahmbhatt et al., U.S. PTO Office Action, U.S. Appl. No. 10/602,021 dated Jul. 25, 2008, 10 pgs.
H. Brahmbhatt et al., U.S. PTO Office Action, U.S. Appl. No. 11/211,098 dated Feb. 24, 2009, 24 pgs.
H. Brahmbhatt et al., U.S. PTO Office Action, U.S. Appl. No. 11/211,098 dated Apr. 24, 2008, 38 pgs.
H. Brahmbhatt et al., U.S. PTO Office Action, U.S. Appl. No. 11/211,098 dated Aug. 7, 2009, 23 pgs.
H. Brahmbhatt et al., U.S. PTO Office Action, U.S. Appl. No. 11/691,698 dated Dec. 24, 2008, 13 pgs.
H. Brahmbhatt et al., U.S. PTO Office Action, U.S. Appl. No. 11/765,635 dated Oct. 6, 2009, 40 pgs.
H. Brahmbhatt et al., U.S. PTO Office Action, U.S. Appl. No. 12/053,197 dated Aug. 25, 2009, 25 pgs.
H.J. Broxterman et al., "Daunomycin Accumulation in Resistant Tumor Cells as a Screening Model for Resistance Modifying Drugs: Role of Protein Binding", Cancer Letters, 1987, vol. 35, pp. 87-95.
Hans J. Dehaard et al., "A Large Non-immunized Human Fab Fragment Phage Library That Permits Rapid Isolation and Kinetic Analysis of High Affinity Antibodies", The Journal of Biological Chemistry vol. 274, No. 26, Issue of Jun. 25, pp. 18218-18230, 1999.
Hao Wu et al., "Small lnterfereing RNA-induced Suppression of MDR1 (P-Glycoprotein) Restores Sensitivity to Multidrug-resistant Cancer Cells", Cancer Research, 63, 1515-1519, Apr. 1, 2003.
Hiroshi Nikaido, "Prevention of Drug Access to Bacterial Targets: Permeability Barriers and Active Efflux", Science, vol. 264, Apr. 15, 1994, pp. 382-388.
Hong-Gang Wang et al., "Bcl-2 interacting protein, BAG-1, binds to and activates the kinase Raf-1", Proc. Natl. Acad. Sci. USA, vol. 93, pp. 7063-7068, Jul. 1996.
Hong et al., Antisense Bc12 Oligonucleotide in Cisplatin-Resistant Bladder Cancer Cell Lines, *BJU International*, vol. 90, pp. 113-117 (2002).
Howard Riezman, "Three clathrin-dependent budding steps and cell polarity", Trends in Cell Biology, Vo. 3, Oct. 1993, pp. 330-332.
Huiqin Shen et al., "Reversal of Multidrug Resistance of Gastric Cancer Cells by Downregulation of TSG101 with TSG101siRNA", Cancer Biology & Therapy, Jun. 2004, pp. 561-565, vol. 3, No. 6.
Ian R. Hart, "Tissue Specific Promoters in Targeting Systemically Delivered Gene Therapy", Seminars in Oncology, 1996, vol. 23, No. 1, pp. 154-158.
Ian Tomlinson et al., "[28] Methods for Generating Multivalent and Bispecific Antibody Fragments", Multivalent and Bispecific Antibody Fragments, Methods in Enzymology, vol. 326, pp. 461-479, 2000.
Igor Dmitriev et al., "Ectodomain of Coxsackievirus and Adenovirus Receptor Genetically Fused to Epidermal Growth Factor Mediates Adenovirus Targeting to Epidermal Growth Factor Receptor-Positive Cells", Journal of Virology, Aug. 2000, vol. 74, No. 15, pp. 6875-6884.
Inder M. Verma et al., "Gene Therapy: Twenty-First Century Medicine", Annu. Rev. Biochem. 2005, 74:711-738.
International Search Report PCT/162008/002984 dated Mar. 26, 2009.
J. H. Hong et al., "Antisense Bc12 oligonucleotide in cisplatin-resistant bladder cancer cell lines," BJU International, vol. 90, (2002), pp. 113-117.
JA Mccubrey, et al., "Enhanced ability of daniplestim and myelopoietin-1 to suppress apoptosis in human hematopoitic cells", Leukemia, 2001, 15, 1204-1216.

Jacquelien C. Pikaar et al., "Opsonic Activities of Surfactant Proteins A and D in Phagocytosis of Gram-Negative Bacteria by Alveolar Macrophages", The Journal of Infectious Diseases, 1994; 172:481-489.
Jane A. Endicott et al., "The Biochemistry of P-Glycoprotein-Mediated Multidrug Resistance1", Annu. Rev. Biochem., 1989, vol. 58, pp. 137-171.
Jane Osbourn et al., "Current methods for the generation of human antibodies for the treatment of autoimmune diseases", Drug Discovery Today, vol. 8, No. 18, Sep. 2003, pp. 845-851.
Jean-Remi Bertrand et al., "Comparison of antisense oligonucleotides and siRNAS in cell culture and in vivo," Biochemical and Biophysical Research Communications, vol. 296, (2002), pp. 1000-1004.
Jeff F. Miller, "[30] Bacterial Transformation by Electroporation", Bacterial Electroporation, Methods in Enzymology, vol. 235, 1994, pp. 375-385.
Jennifer A. Macdiarmid et al., "Bacterially derived 400 nm particles for encapsulation and cancer cell targeting of chemotherapeutics", Cancer Cell, vol. 11, No. 5, May 1, 2007, pp. 431-445.
Jennifer A. Macdiarmid et al., "Reversal of drug resistance in cancer: Target delivery of siRNA and drugs in vivo via biologically derived nanoparticles", Proceedings of the American Association for Cancer Research Annual Meeting, vol. 48, Apr. 2007, p. 1371, XP001537093 & 98$^{TH}$ Annual Meeting for the American-Association-For-Cancer-Research; Los Angeles, CA, USA; Apr. 14-18, 2007.
Joacim Elmen et al., "Locked nucleic acid (LNA) mediated improvements in siRNA stability and functionality", Nucleic Acids Research 2005, vol. 33, No. 1, 439-447.
Joanna B. Opalinska et al., "Nucleic-Acid Therapeutics: Basic Principles and Recent Applications", Nature Reviews, Drug Discover, vol. 1, Jul. 2002, pp. 503-514.
John B.B. Ridgway et al., "Knobs-into-holes engineering of antibody CH3 domains for heavy chain heterodimerization", Protein Engineering vol. 9, No. 7, pp. 617-621, 1996.
John J. Hunter et al., "Functional Dissection of the Human Bcl2 Protein: Sequence Requirements for Inhibition of Apoptosis", Molecular and Cellular Biology, 1996, vol. 16, No. 3, pp. 877-883.
John J. Rossi et al., "Ribozymes as Anti-HIV-1 Therapeutic Agents: Principles, Applications & Problems", AIDS Research & Human Retroviruses, vol. 8, No. 2, 1992, pp. 183-189.
John Marshall, "Carcinoembryonic Antigen-Based Vaccines", Seminars in Oncology, vol. 30, No. 3, Supp. 8, Jun. 2003, pp. 30-36.
John N. Reeve et al. "Bacteriophage SPO1-Induced Macromolecular Synthesis in Minicells of Bacillus subtilis", Journal of Virology, vol. 15, No. 6, Jun. 1975, pp. 1308-1316.
Jörg Kleeff et al., "Targeting of suicide gene delivery in pancreatic cancer cells via FGF receptors", Cancer Gene Therapy, 2002, vol. 9, pp. 522-532.
Juliana M. Layzer et al., "In vivo activity of nuclease-resistant siRNAs", RNA (2004) 10:766-771.
Karagiannis & Anderson (2009) "Minicells overcome tumor drug-resistance" Nature Biotechnology 27(7):620-621.
Katsunori Yanagihara et al., "Effects of short interfering RNA against methicillin-resistant *Staphylococcus aureus* coagulase in vitro and in vivo", The Journal of Antimicrobial Chemotherapy, Jan. 2006, vol. 57, No. 1, Jan. 2006, pp. 122-126, XP002518418.
Keiko Antoku et al., Isolation of Bcl-2 Binding Proteins that Exhibit Homology with BAG-1 and Suppressor of Death Domains Protein, Biochemical and Biophysical Research Communications, 286, pp. 1003-1010 (2001).
Keith Ireton et al., "spo0J Is Required for Normal Chromosome Segregation as well as the Initiation of Sporulation in Bacillus subtilis", Journal of Bacteriology, 1994, vol. 176, No. 17, pp. 5320-5329.
Kenneth E. Sawin et al., "Mutations in the kinesin-like protein Eg5 disrupting localization to the mitotic spindle", Cell Biology, Proc. Natl. Acad. Sci. USA, vol. 92, pp. 4289-4293, May 1995.
Klaus Strebhardt et al., "Targeting polo-like kinase 1 for cancer therapy", Nature Reviews, Cancer, vol. 6, Apr. 2006, pp. 321-330.
Kristen Sandvig et al., "Endocytosis without clathrin", Trends in Cell Biology, vol. 4, Aug. 1994, pp. 275-277.

(56) References Cited

OTHER PUBLICATIONS

Kristi G. Bache et al., "New EMBO Member's Review: Defective downregulation of receptor tyrosine kinases in cancer", The EMBO Journal (2004) 23, 2707-2712.

L. R. Kelland, "Of mice and men": values and liabilities of the athymic nude mouse model in anticancer drug development, European Journal of Cancer, vol. 40, (2004), pp. 827-836.

Lebedeva, et al., Antisense Oligonucleotides: Promise and Reality, Annu. Rev. Pharmacol. Toxicol. (2001), vol. 41, pp. 403-419.

Leng et al. (2009) "Advances in Systemic siRNA Delivery" Drugs Future 34(9):721.

Leoni A. Kunz-Schughart et al., "The Use of 3-D Cultures for High-Throughput Screening: The Multicellular Spheriod Model," Journal of Biomolecular Screening, vol. 9, (2004), pp. 273-285.

Letter from Knobbe Martens Olson & Bear LLP dated Feb. 26, 2010.

Lutz Riechmann et al., "Reshaping human antibodies for therapy", Nature, vol. 332, Mar. 24, 1988, pp. 323-327.

M. Singh, "Transferring as a Targeting Ligand for Liposomes and Anticancer Drugs", Current Pharmaceutical Design 1999, 5, 443-451.

M.C. Hung et al., "16-Development of Clinical Trial of E1A Gene Therapy Targeting HER-2lneu-Overexpressing Breast and Ovarian Cancer", Cancer Gene Therapy: Past Achievements and Future Challenges, 2000, pp. 171-180.

MacDiarmid et al. (2009) "Sequential treatment of drug-resistant tumors with targeted minicells containing siRNA or a cytotoxic drug" Nature Biotechnology 27(7):643-651.

Maha M. Katabi et al., "Hexokinase Type II: A Novel Tumor-Specific Promoter for Gene-Targeted Therapy Differentially Expressed and Regulated in Human Cancer Cells", Human Gene Therapy, 1999, vol. 10, pp. 155-164.

Manisha P. Desai et al., "The Mechanism of Uptake of Biodegradable Microparticles in Caco-2 Cells is Size Dependent", Pharmaceutical Research, vol. 14, No. 11, 1997, pp. 1568-1573.

Mark Forbes, "Crossflow Microfiltration", Australian Journal of Biotechnology, 1987, vol. 1, No. 1, pp. 30-33.

Mark S. Duxbury et al., "siRNA Directed Against c-Src Enhances Pancreatic Adenocarcinoma Cell Gemcitabine Chemosensitivity", American College of Surgeons, 2004, vol. 198, No. 6, pp. 953-959.

Markus Bredel, "Anticancer drug resistance in primary human brain tumors", Brain Research Reviews, 2001, vol. 35, pp. 161-204.

Martin J. Glennie et al., "Preparation and Performance of Bispecific F(ab'y)2 Antibody Containing Thioether-Linked Fab'y Fragments", The Journal of Immunology, vol. 139, 2367-2375, No. 7, Oct. 1, 1987.

Martin Thurnher et al., "Carbohydrate receptor-mediated gene transfer to human T leukaemic cells", Glycobiology vol. 4, No. 4, pp. 429-435, 1994.

Martine Verhoeyen et al., "Reshaping Human Antibodies: Grafting an Antilysozyme Activity", Science, vol. 239, pp. 1534-1536, Mar. 25, 1988.

Marzia B. Gariboldi et al., "Molecular determinants of intrinsic resistance to doxorubicin in human cancer cell lines", International Journal of Oncology, 2003, vol. 22, pp. 1057-1064.

Masaaki Wachi et al., "New mre Genes mreC and mreD, Responsible for Formation of the Rod Shape of *Escherichia coli* Cells", Journal of Bacteriology, vol. 171, No. 12, Dec. 1989, pp. 6511-6516.

Masahisa Watarai et al., "Interaction of Ipa Proteins of Shigella flexneri with a5ß1 Integrin Promotes Entry of the Bacteria into Mammalian Cells", J. Exp. Med. vol. 183, Mar. 1996, pp. 991-999.

McNamara et al. (2006) "Cell type-specific delivery of siRNAs with aptamer-siRNA chimeras" Nature Biotechnology 24(8):1005-1015.

Michael A. Gosselin et al., "Folate receptor-targeted liposomes as vectors for therapeutic agents", Biotechnology Annual Review, vol. 8, pp. 103-131, 2002.

Michael D. Sheets et al., "Efficient construction of a large nonimmune phage antibody library: The production of high-affinity human single-chain antibodies to protein antigens", Proc. Natl. Acad. Sci. USA, vol. 95, pp. 6157-6162, May 1998.

Michael J. Mccluskie et al., "Route and Method of Delivery of DNA Vaccine Influence Immune Responses in Mice and Non-Human Primates," Molecular Medicine, vol. 5, (1999), pp. 287-300.

Michael M. Gottesman et al., "Multidrug Resistance in Cancer: Role of ATP-Dependent Transporters", Nature Reviews/Cancer vol. 2, Jan. 2002, pp. 48-58.

Michael Sattler et al., "Structure of Bcl-xL-Bak Peptide Complex: Recognition Between Regulators of Apoptosis", Science, vol. 275, Feb. 14, 1997, pp. 983-986.

Michael T. McManus et al., "Gene Silencing in Mammals by Small Interfering RNAs", Nature Reviews, Genetics, vol. 3, Oct. 2002, pp. 737-747.

Michele Carbone et al., "Multistep and multifactorial carcinogenesis: when does a contributing factor become a carcinogen?," Seminars in Cancer Biology, vol. 14, (2004) pp. 399-405.

Michele De Palma et al., "In Vivo Targeting of Tumor Endothelial Cells by Systemic Delivery of Lentiviral Vectors," Human Gene Therapy, vol. 14, Aug. 10, 2003, pp. 1193-1206.

MK White et al., "Suppression of apoptosis: role in cell growth and neoplasia", Leukemia (2001) 15, 1011-1021.

Monique Frain et al., "Binding of a Liver-Specific Factor to the Human Albumin Gene Promoter and Enhancer", Molecular and Cellular Biology, 1990, pp. 991-999.

Motoi Hanada et al., "Structure-Function Analysis of Bcl-2 Protein", The Journal of Biological Chemistry, vol. 270, No. 20, Issue of May 19, 1995, pp. 11962-11969.

Mouldy Sioud, "Therapeutic siRNAs", Trends in Pharmacological Sciences, vol. 25, No. 1, Jan. 2004, pp. 22-28.

Mukesh K. Nyati et al., "Radiosensitization by Pan ErbB Inhibitor CI-1033 in Vitro and in Vivo", Clinical Cancer Research, vol. 10, 691-700, 2004.

Natasha J. Caplen et al., "Short Interfering Rna (siRNA)-Mediated RNA Interference (RNAi) in Human Cells", Annals New York Academy of Sciences, 2003, 1002, pp. 56-62.

Natasha J. Caplen, "RNAi as a gene therapy approach", Expert Opin. Biol. Ther., 2003, Vo. 3, No. 4, pp. 575-586.

Neeltje A. Kootstra et al., "Gene Therapy with Viral Vectors", Annu. Rev. Pharmacol. Toxicol. 2003, 43:413-439.

Nikaido, Hiroshi, "Prevention of drug access to bacterial targets: permeability barriers and active efflux." Science. 1994. vol. 264. pp. 382-388.

Non Final Office Action U.S. Appl. No. 12/053,197 dated Aug. 25, 2009.

Non-Final Office Action U.S. Appl. No. 11/211,098 dated Sep. 23, 2010.

Non-Final Office Action U.S. Appl. No. 12/053,197 dated Mar. 2, 2009.

Notice of Reasons for Rejection Japanese Patent Application No. 2007-529046 dated Jun. 28, 2011.

Olivier Fardel et al., "The P-Glycoprotein Multidrug Transporter", Gen. Pharmac., 1996, vol. 27, No. 8, pp. 1283-1291.

P. Borst et al., "Mammalian ABC Transporters in Health and Disease", Annu. Rev. Biochem. 2002, 71:537-592.

Panja et al., "How does plasmid DNA penetrate cell membranes in artificial transformation process of *Escherichia coli*." Molecular Membrane Biology. 2008. vol. 25 No. 5. pp. 411-422.

Pascal Peschard, "Escape from Cbl-mediated downregulatation: A recurrent theme for oncogenic deregulation of receptor tyrosine kinases", Cancer Cell, Jun. 2003, vol. 3, pp. 519-523.

Patrick J. Paddison et al., "Short hairpin RNAs (shRNAs) induce sequence-specific silencing in mammalian cells", Genes and Development 16:948-958, 2002.

Paul Carter, "Improving the Efficacy of Antibody-Based Cancer Therapies", Nature Reviews/Cancer, 2001, vol. 1, pp. 118-129.

Peter J. Hudson et al., "Engineered antibodies", Nature Medicine, 2003, vol. 9, No. 1, pp. 129-134.

Peter Pack et al., "Miniantibodies: Use of Amphipathic Helices to Produce Functional, Flexibly Linked Dimeric Fv Fragments with High Avidity in *Escherichia coli*", American Chemical Society, vol. 31, No. 6, Feb. 1992, pp. 1579-1584.

(56) References Cited

OTHER PUBLICATIONS

Peter T. Jones et al., "Replacing the complementarity-determining regions in a human antibody with those from a mouse", Nature, 1986, vol. 321, pp. 522-525.
Petra Anne Levin et al., "Identification of Bacillus subtilis Genes for Septum Placement and Shape Determination", Journal of Bacteriology, 1992, vol. 174, No. 21, pp. 6717-6728.
Philip S. Stewart et al., "Genetic and Morphological Characterization of an *Escherichia coli* Chromosome segregation Mutant", Journal of Bacteriology, Jul. 1992, vol. 174, No. 13, pp. 4513-4516.
Phillip A. Sharp, "RNA interference—2001", Genes & Development 15: 485-490, 2001.
Phillip D. Zamore et al., "RNAi: Double-Stranded RNA Directs the ATP-Dependent Cleavage of mRNA at 21 to 23 Nucleotide Intervals", Cell., vol. 101, 25-33, Mar. 31, 2000.
Phillip D. Zamore, "Ancient Pathways Programmed by Small RNAs", Science, vol. 296, May 17, 2002, pp. 1265-1269.
Piet A. J. Deboer et al., "Roles of MinC and MinD in the Site-Specific Septation Block Mediated by the MinCDE System of *Escherichia colo*", Journal of Bacteriology, Jan. 1992, vol. 174, No. 1, pp. 63-70.
PR Dash et al., "Factors affecting blood clearance and in vivo distribution of polyelectrolyte complexes for gene delivery", Gene Therapy (1999)6, pp. 643-650.
R. L. Juliano et al., "A Surface Glycoprotein Modulating Drug Permeability in Chinese Hamster Ovary Cell Mutants", Biochimica et Biophysica Acta., 1976, vol. 455, pp. 152-162.
R.I. Nicholson et al., "EGFR and cancer prognosis", European Journal of Cancer 37 (2001) S9-S15.
Raj K. Batra et al., "Receptor-mediated gene delivery employing lectin-binding specificity", Gene Therapy, 1994, vol. 1, No. 4, pp. 255-260.
Ralf C. Bargou et al., Expression of the bcl-2 Gene Family in Normal and Malignant Breast Tissue: Low bax-α Expression in Tumor Cells Correlates With Resistance Towards Apoptosis, International Journal of Cancer, 1995, vol. 60, pp. 854-859.
Raymond J. MacDonald, "Expression of the Pancreatic Elastase I Gene in Transgenic Mice", Hepatology, vol. 17, No. 1, pp. 42S-51S, 1987.
Richard A. Collins et al., "Reaction Conditions and Kinetics of Self-Cleavage of a Ribozyme Derived from Neurospora VS RNA\", Biochemistry, 1993, vol. 32, No. 11, pp. 2795-2799.
Richard J. Klasa et al., "Eradication of Human Non-Hodgkin's Lymphoma in SCID Mice by BCL-2 Antisense Oligonucleotides Combined with Low-Dose Cyclophosphamide", Clin. Cancer Res. 2000, 6:2492-2500.
Richard J. Stockert, "The Asialoglycoprotein Receptor: Relationships Between Structure, Function and Expression", Physiological Reviews, vol. 75, No. 3, Jul. 1995, pp. 591-609.
Robert A. Britton et al., "Characterization of a prokaryotic SMC protein involved in chromosome partitioning", Genes & Development, 1998, vol. 12, pp. 1254-1259.
Robert S. Kerbel, "What is the optimal rodent model for anti-tumor drug testing'?," Cancer and Metastasis Reviews, vol. 17, (1999), pp. 301-304.
Roger Heim et al., "Wavelength mutations and posttranslational autoxidation of green fluorescent protein", Proc. Natl. Acad. Sci. USA, 1994, vol. 91, pp. 12501-12504.
Rosalind C. Lee et al., "The C. elegans Heterochronic Gene lin-4 Encodes Small RNAs with Antisense Complementarity to lin-14", Cell, vol. 75, Dec. 3, 1993, pp. 843-854.
S. Dübel et al., "Bifunctional and multimeric complexes of streptavidin fused to single chain antibodies (scFv)", Journal of Immunological Methods, 1995, vol. 178, pp. 201-209.
S. Hacein-Bey-Abina et al., "LMO2-Associated Clonal T Cell Proliferation in Two Patients after Gene Therapy for SCID-X1", Science, vol. 302, Oct. 17, 2003, pp. 415-419.
S.P.C. Cole et al., "Overexpression of a Transporter Gene in a Multidrug-Resistant Human Lung Cancer Cell Line", Science, 1992, vol. 258, pp. 1650-1654.

Samuel D. Wright et al., "Interferon-γ Depresses Binding of Ligand by C3b and C3bi Receptors on Cultured Human Monocytes an Effect Reversed by Fibronectin," J. Exp. Med. vol. 163, May 1986, 1245-1259.
Sayda M. Elbashir et al., "Duplexes of 21-nucleotide RNAs mediate RNA interference in cultured mammalian cells", Nature, 2001, vol. 411, pp. 494-498.
Sayda M. Elbashir et al., "RNA interference is mediated by 21- and 22-nucleotide RNAs", Genes & Development, 2001, vol. 15, pp. 188-200.
Sean D. Conner et al., "Regulated Portals of Entry into the Cell", Nature, vol. 422, Mar. 6, 2003, pp. 37-44.
Sheri A. Kostelny et al., Formation of a Bispecific Antibody by the Use of Leucine Zippers, The Journal of Immunology, 1992, vol. 148, No. 5, pp. 1547-1553.
Shi-Yong Sun et al., "Overexpression of Bcl2 Blocks TNF-Related Apoptosis-Inducing Ligand (TRAIL)-Induced Apoptosis in Human Lung Cancer Cells", Biochemical and Biophysical Research Communications 280, pp. 788-797, 2001.
Shi-zhen Hu et al., "Minibody: A Novel Engineered Anti-Carcinoembryonic Antigen Antibody Fragment (Single-Chain Fv-CH3) Which Exhibits Rapid, High-Level Targeting of Xenografts", Cancer Research, 1996, vol. 56, pp. 3055-3061.
Shuji Kurane et al., "Targeted Gene Transfer for Adenocarcinoma Using a Combination of Tumor-specific Antibody and Tissue-specific Promoter", Jpn. J. Cancer Res., 1998, vol. 89, pp. 1212-1219.
Soengas, et al., Apoptosis and melanoma chemoresistance, Oncogene (2003), vol. 22, pp. 3138-3151.
Sorim Choung et al., "Chemical modification of siRNAs to improve serum stability without loss of efficacy", Biochemical and Biophysical Research Communications 342 (2006), 919-927.
Sota Hiraga et al., "Chromosome Partitioning in *Escherichia coli*: Novel Mutants Producing Anucleate Cells", Journal of Bacteriology, 1989, vol. 171, No. 3, pp. 1496-1505.
Stephen L. Eck et al., "Gene-Based Therapy," Chapter 5, Goodman & Gilman's the Pharmacological Basis of Therapeutics, (1996), pp. 77-102.
Steven E. Raper et al., "Fatal systemic inflammatory response syndrome in a ornithine transcarbamylase deficient patient following adenoviral gene transfer", Molecular Genetics and Metabolism 80 (2003) 148-158.
Suhail Ayesh et al., "Co-operative, competitive and non-competitive interactions between modulators of P-glycoprotein", Biochimica et Biophysica Acta, 1996,1316, pp. 8-18.
Suhail Ayesh et al., "Reversal of P-glycoprotien is greatly reduced by the presence of plasma but can be monitored by an ex vivo clinical assay", Anti-Cancer Drugs, 1996, 7, pp. 678-686.
Supplementary European Search Report EP 05 80 6875 dated Jan. 26, 2009.
Suresh V. Ambudkar et al., "Biochemical, Cellular and Pharmacological Aspects of the Multidrug Transporter", Annu. Rev. Pharmacol. Txicol. 1999, 39: 361-398.
Suzanne Cory, "Regulation of Lymphocyte Survival by the BCL-2 Gene Family", Annu. Rev. Immunol., 1995, vol. 13, pp. 513-543.
Szabolcs Modok et al., "Modulation of multidrug resistance efflux pump activity to overcome chemoresistance in cancer", Current Opinion in Pharmacology 2006, 6:350-354.
T. Litman et al., "From MDR to MXR: new understanding of multidrug resistance systems, their properties and clinical significance" CMLS, pp. 931-959.
Takaaki Sato et al., "Interactions among members of the Bcl-2 protein family analyzed with a yeast two-hybrid system", Proc. Natl. Acad. Sci. USA, vol. 91, pp. 9238-9242, Sep. 1994.
Tarun M. Kapoor et al., "Probing Spindle Assembly Mechanisms with Monastrol, a Small Molecule Inhibitor of the Mitotic Kinesin, Eg5", The Journal of Cell Biology, vol. 150, No. 5; Sep. 4, 2000, pp. 975-988.
Thijn R. Brummelkamp et al., "A System for Stable Expression of Short Interfering RNAs in Mammalian Cells", Science, 2002, vol. 296, pp. 550-553.

(56) References Cited

OTHER PUBLICATIONS

Thijn R. Brummelkamp et al., "Stable suppression of tumorigenicity by virus-mediated RNA interference", Cancer Cell, Sep. 2002, vol. 2002, pp. 243-247.
Thomas L. Hale et al., "Characterization of Virulence Plasmids and Plasmid-Associated Outer Membrane Proteins in Shigella flexneri, Shigella sonnei, and *Escherichia coli*", Infection and Immunity, Apr. 1983, vol. 40, No. 1, pp. 340-350.
Thomas Litman et al., "The multidrug-resistant phenotype associated with overexpression of the new ABC half-transporter, MXR (ABCG2)", Journal of Cell Science, 2000, vol. 113, pp. 2011-2021.
Thomas P. Miller et al., "P-Glycoprotein Expression in Malignant Lymphoma and Reversal of Clinical Drug Resistance with Chemotherapy Plus High-Dose Verapamil", Journal of Clinical Oncology, vol. 9, No. 1, 1991; pp. 17-24.
Thomas U Mayer et al., "Small Molecule Inhibitor of Mitotic Spindle Bipolarity Identified in a Phenotype-Based Screen", Science, vol. 286, Oct. 29, 1999, pp. 971-974.
Tibor Pal et al., "Plasmid-Associated Adherence of Shigella flexneri in a HeLa Cell Model", Infection and Immunity, Aug. 1989, vol. 57, No. 8, pp. 2580-2582.
Timothy A. Vickers et al., "Efficient Reduction of Target RNAs by Small Interfering RNA and Rnase H-dependent Antisense Agents", The Journal of Biological Chemistry, vol. 278, No. 9, Issue of Feb. 2, 2003, pp. 7108-7118.
Tohru Hosida et al., "Gene Therapy for Pancreatic Cancer Using an Adenovirus Vector Encoding Soluble flt-1 Vascular Endothelial Growth Factor Receptor", Pancreas, vol. 25, No. 2, pp. 111-121.
Tristan J. Vaughan et al., "Human antibodies by design", Nature Biotechnology, vol. 16, Jun. 1998, pp. 535-539.
Tristan J. Vaughan et al., "Human Antibodies with Sub-nanomolar Affinities Isolated from a Large Non-immunized Phage Display Library", Nature Biotechnology vol. 14, Mar. 1996, pp. 309-314.
U.S. Office Action for U.S. Appl. No. 12/980,781, dated Sep. 4, 2012.
Volker Wacheck et al., Small Interfering RNA Targeting Bcl-2 Sensitizes Malignant Melanoma, Oligonucleoties 13: 393-400, (2003).
Weikang Tao et al., "Induction of apoptosis by an inhibitor of the mitotic kinesin KSP requires both activation of the spindle assembly checkpoint and mitotic slippage", Cancer Cell, Jul. 2005, vol. 8, pp. 49-59.
Whitehead et al., "Knocking down barriers: advances in siRNA delivery." Nature Reviews Drug Discovery 8. 2009. pp. 129-138.
William F. Scherer et al., "Studies of the Propagation in Vitro of Poliomyelitis Viruses", Journal of Experimental Medicine, vol. 97, No. 5, pp. 695-710 (1953).
William F. Scherer M.D. et al., "The Viral Range In Vitro Of a Malignant Human Epithelial Cell (Strain Hela, Gey)—III. Studies with Pseudolymphocytic Choriomeningitus Virus General Discussion", American Journal of Pathology, Jan.-Feb. 31(1): 31-39 (1954).
William R. Sellers et al., "Apoptosis and cancer drug targeting", The Journal of Clinical Investigation, Dec. 1999, vol. 104, No. 12, pp. 1655-1661.
Wu et al., Small Interfering RNA-induced Suppression of MDR1 (P-Glycoprotein) Restores Sensitivity to Multidrug-resistant Cancer Cells, *Cancer Research*, vol. 63, pp. 1515-1519 (2003).
Xing-Jie Liang et al., "Mislocalization of Membrane Proteins Associated with Multidrug Resistance in Cisplatin-resistant Cancer Cell Lines", Cancer Res. 2003, 63:5909-5916.
Ya-Lin Chiu et al., "siRNA function in RNAi: A chemical modification analysis", RNA (2003) 9:1034-1048.
Yanagihara et al., "Effects of short interfering RNA against methicillin-resistant *Staphylococcus aureus* coagulase in vitro and in vivo." Journal of Antimicrobial Chemotherapy. 2006. vol. 57. pp. 122-126.
Yi Lu et al., "Delivery of adenoviral vectors to the prostate for gene therapy," Cancer Gene Therapy, vol. 6, No. 1, (1999), pp. 64-72.
Yoshio Okada et al., "Cytoplasmic Axial Filaments in *Escherichia coli* Cells: Possible Function in the Mechanism of Chromosome Segregation and Cell Division", Journal of Bacteriology, vol. 176, No. 3, Feb. 1994, pp. 917-922.

Yoshio Okada et al., "Possible function of the cytoplasmic axial filaments in chromosomal segregation and cellular division of *Escherichia coli*", Science Progress (1993/94), 77 (3/4) 253-264.
Zhenfeng Duan et al., "Inhibition of ABCB1 (MDR1) and ABCB4 (MDR3) expression by small interfering RNA and reversal of paclitaxel resistance in human ovarian cancer cells", Molecular Cancer Therapeutics, 2004, vol. 3, No. 7, pp. 833-838.
Zhe-Sheng Chen et al., "Reversal of Drug Resistance Mediated by Multidrug Resistance Protein (MRP) 1 by Dual Effects of Agosterol A on MRP1 Function", Int. J. Cancer, 2001, vol. 93, pp. 107-113.
Zonglin Hu et al., "Topological regulation of cell division in *Escherichia coli* involves rapid pole to pole oscillation of the division inhibitor MinC under the control of MinD and MinE", Molecular Microbiology, 1999, vol. 34, No. 1, pp. 82-90.
Notice of Allowance issued in related U.S. Appl. No. 12/053,197, dated Jan. 16, 2014.
Notice of Allowance issued in related U.S. Appl. No. 12/980,781, dated Oct. 30, 2013.
Notice of Allowance issued in related U.S. Appl. No. 12/211,098, dated Nov. 14, 2013.
European Search Report issued in related European Patent Application No. 12178465, dated Jul. 11, 2013.
Geller et al., "Antisense Phosphorodiamidate Morpholino Oligomer Inhibits Viability of *Escherichia coli* in Pure Culture and in Mouse Peritonitis," *Journ. of Antimicrobial Chemotherapy*, vol. 55, pp. 983-988 (2005).
Harth et al., "Treatment of Mycobacterium Tuberculosis with Antisense oligonucleotides to glutamine synthetase mRNA inhibits glutamine synthetase activity, formation of the poly-L-glutamate/glutamine cell wall structure, and bacterial replication," *Proceedings of the National Academy of Sciences of the USA*, vol. 97, No. 1, pp. 418-423 (2000).
MacDiarmid et al., "Reversal of drug resistance in cancer: Target delivery of siRNA and drugs in vivo via biologically derived nanoparticles," *Proceedings of the American Association for Cancer Research Annual Meeting*, vol. 48, p. 1371 (2007).
MacDiarmid et al., "Bacterially derived 400 nm particles for encapsulation and cancer cell targeting of chemotherapeutics," *Cancer Cell*, vol. 11, No. 5, pp. 431-445 (2007).
Non-Final Office Action issued in related U.S. Appl. No. 12/980,781, dated Jul. 25, 2013.
Notice of Allowance issued in related U.S. Appl. No. 12/980,781, dated Mar. 18, 2013.
Final Office Action issued in related U.S. Appl. No. 12/980,781, dated Feb. 4, 2013.
Office Action cited in related U.S. Appl. No. 13/912,890, dated Aug. 19, 2014.
Office Action cited in related U.S. Appl. No. 14/207,304, dated Aug. 19, 2014.
Notice of Allowance issued in related U.S. Appl. No. 13/912,890, dated Sep. 15, 2014.
Office Action cited in related U.S. Appl. No. 14/207,304, dated Nov. 7, 2014.
Notice of Allowance issued in related U.S. Appl. No. 14/207,304, dated Feb. 25, 2015.
European Search Report issued in related European Patent Application No. 15 150 129.3, dated Apr. 2, 2015.
Office Action issued in related U.S. Appl. No. 14/744,848, dated Feb. 21, 2017.
Giacalone, et al., Immunization with non-replicating *E. coli* minicells delivering both protein antigen and DNA protects mice from lethal challenge with lymphocytic choriomeningitis virus, *Vaccine*, vol. 25, No. 12, pp. 2279-2287 (2006).
Search Report and Written Opinion issued in related Singapore Patent Application No. 10201507969P, dated Mar. 27, 2017.
Office Action issued in co-pending U.S. Appl. No. 15/604,555, dated Nov. 2, 2018.
Office Action issued in related U.S. Appl. No. 14/744,848, dated Feb. 9, 2018.
Office Action issued in co-pending Chinese Patent Application No. 201610277472.0, dated Nov. 6, 2018.
Notice of Allowance issued in co-pending U.S. Appl. No. 16/156,856, dated Apr. 8, 2019.

(56) References Cited

OTHER PUBLICATIONS

Office Action issued in co-pending U.S. Appl. No. 15/604,555, dated Feb. 12, 2019.
Notice of Allowance issued in co-pending U.S. Appl. No. 15/604,555, dated May 22, 2019.

DELIVERING FUNCTIONAL NUCLEIC ACIDS TO MAMMALIAN CELLS VIA BACTERIALLY-DERIVED, INTACT MINICELLS

This application is a continuation of U.S. patent application Ser. No. 14/983,126, filed Dec. 29, 2015, which is a divisional of U.S. patent application Ser. No. 14/152,979, filed Jan. 10, 2014, now U.S. Pat. No. 9,242,007, which is a divisional of U.S. patent application Ser. No. 11/211,098, filed Aug. 25, 2005, now U.S. Pat. No. 8,691,963, which claims priority from U.S. Patent Application No. 60/604,433, filed Aug. 26, 2004. The contents of these applications are incorporated herein by reference in their entirety.

BACKGROUND OF THE INVENTION

The instant application contains a Sequence Listing which has been submitted electronically in ASCII format and is hereby incorporated by reference in its entirety. Said ASCII copy, created on Jul. 8, 2014, is named 060348-0318 SL.txt and is 871 bytes in size.

The present invention relates to ongoing efforts to achieve effective delivery of functional nucleic acids to mammalian cells. More specifically, the invention relates to using bacterial minicell vectors to deliver functional nucleic acids to mammalian cells. The invention has particular utility for eliminating drug resistance, especially in the context of cancer and AIDS therapy, for promoting apoptosis and for countering neoplasticity in targeted cells.

Recent advances have highlighted a variety of techniques for introducing functional nucleic acids into cells. For example, liposome-based transfection methods can deliver exogenously produced nucleic acids. Such an exogenous approach has the drawback, however, of effecting only transient inhibition of a target. Additionally, liposomes are unstable in vivo. As an alternative to delivery of exogenously produced nucleic acids, vectors can deliver plasmids that encode functional nucleic acids, which are produced endogenously. The viral vectors currently useful for this purpose, however, poses serious safety concerns. Illustrative problems include recombination with wild-type viruses, insertional and oncogenic potential, virus-induced immunosuppression, limited capacity of the viral vectors to carry large segments of DNA, reversion to virulence of attenuated viruses, difficulties in recombinant virus manufacture and distribution, low stability, and adverse reactions, such as an inflammatory response, caused by existing immunity. An approach that obviated these problems would offer significant benefit in making delivery of functional nucleic acids safer and more effective.

An effective method of delivering functional nucleic acids would be particularly beneficial for reversing drug resistance. Mammalian cells employ a variety of biological processes to resist drugs, which poses a major obstacle to the successful treatment of cancer. Similarly, drug resistance limits the efficacy of HIV treatment, particularly to highly active antiretroviral therapy (HAART), which is based on a combination of nucleoside reverse transcriptase inhibitors (NRTIs) and protease inhibitors (PIs) or a non-nucleoside reverse transcriptase inhibitor (NNRTI).

Clinical tumor resistance to chemotherapy can be intrinsic or acquired. Intrinsic resistance exists at the time of diagnosis in tumors that fail to respond to first-line chemotherapy. Acquired resistance occurs in tumors that may respond well to initial treatment, but exhibit a resistant phenotype upon recurrence. Such tumors gain resistance both to previously used drugs and to new drugs, including drugs with different structures and mechanisms of action. The term MDR (multidrug resistance) describes this phenomenon in which tumor cells become cross-resistant to several structurally unrelated drugs after exposure to a single drug.

The mechanisms for multi-drug resistance are complex and multifactorial, owing largely to the high level of genomic instability and mutations in cancer cells. Exemplary mechanisms are drug inactivation, extrusion of drug by cell membrane pumps, decreased drug influx, mutations of drug targets and failure to initiate apoptosis (Bredel, 2001; Chen et al., 2001; White and McCubrey, 2001; Sun et al., 2001).

Drug extrusion is particularly common, and can result from over-expression of membrane-associated proteins that pump drugs from the intracellular to the extracellular environment. Such pumps often are members of the ATP-binding cassette (ABC) transporter superfamily (Doige et al., 1993). P-glycoprotein (Pgp) is one such example, and is a major contributor to MDR in a variety of cancer cells (Endicott et al., 1989; Litman et al., 2001). Other examples include the MDR-associated protein (MRP; Cole et al., 1992), breast cancer resistance protein (BCRP; Litman et al., 2000), and lung resistance-related protein (LRP; a major vault protein; Scheffer et al., 2000). Other multidrug transporter proteins also have been identified in cancer cells (Gottesman et al., 2002) and in pathogenic microorganisms (Van Bambeke et al., 2000).

Resistance to apoptosis (programmed cell death) of tumor cells induced by cytotoxic agents and radiation (Sellers and Fisher, 1999) is another common mechanism. This mechanism frequently involves over-expression of anti-apoptotic proteins, such as B-cell leukemia protein 2 (Bcl-2), Bcl-$X_L$, Bcl-W, A1/Bfl1, Mcl-1 and mutations in the p53 protein. Although a precise understanding of how proteins like Bcl-2 exerts their anti-apoptotic effects remains elusive, the proteins are over-expressed in many cancers including colorectal, prostate, and breast cancers (Hanada, et al., 1995; Bakhshi et al., 1985; Wang et al., 1996). Increased expression of the transcription factor nuclear factor kappa B (NF-κB) also is a major mechanism for tumor cells to acquire chemotherapy resistance (Wang et al., 1999).

Drugs to counter MDR have been identified, such as drugs that block the action of P-glycoprotein (List et al., 1993; Miller et al., 1991; Wishart et al., 1992). Many such drugs were ineffective in clinical trials, however, because they bound to the plasma of patients, could not reach their destination (Ayesh et al., 1996a; Broxterman et al., 1987; Lehnert et al., 1996) and were toxic to normal cells. The use of functional nucleic acids to counter MDR also has been attempted. Yet, as noted above, existing vectors for this purpose are unstable or toxic, or they pose other serious safety issues, which hamper their use in humans (Sioud, 2004).

Accordingly, a continuing need exists for tools and methods for delivering functional nucleic acids that reduce drug resistance, promote apoptosis, and counter neoplasticity in target cells.

SUMMARY OF THE INVENTION

To address these and other needs, the present invention provides, in one aspect, a method of delivering a functional nucleic acid, comprising (a) providing an intact minicell that contains a functional nucleic acid molecule or contains a plasmid comprising a segment that encodes a functional nucleic acid molecule, then (b) bringing the minicell into contact with a target mammalian cell, such that the mammalian cell engulfs the minicell. Following engulfment of the minicell, the functional nucleic acid molecule is released into the cytoplasm, transported to the nucleus and expressed by the target cell. The aforementioned plasmid also may contain a regulatory element, such as a promoter, a terminator, an enhancer or a signal sequence that is operably linked to the segment that encodes a functional nucleic acid molecule. It is particularly advantageous for the plasmid to comprise a promoter that is dependent on either RNA polymerase (pol) II or pol III, such as the RNA III polymerase promoters human 7SK, H1 and U6. Further, the plasmid may contain a reporter element, such as a nucleic acid segment coding for green fluorescent protein. Contact between the minicell and the mammalian cell may be in vitro or in vivo.

In relation to this invention, the category of "functional nucleic acids" encompasses: siRNA molecules, including shRNA molecules; miRNA molecules, antisense molecules; and ribozyme molecules. Preferably, the functional nucleic acid molecule targets the gene or transcript of a protein that promotes drug resistance, inhibits apoptosis, or contributes to a neoplastic phenotype. Particularly useful targets that contribute to drug resistance include ATP binding cassette transporters such as P-glycoprotein, MDR-2, MDR-3, BCRP, APT11a and LRP. Particularly useful targets that contribute to apoptosis resistance include Bcl-2 (B cell leukemia/lymphoma), Bcl-$X_L$, A1/Bfl 1, focal adhesion kinase and p53 mutant protein. Other useful targets are oncogenic proteins and mutant tumor suppressor proteins.

In another aspect, the invention provides a method of overcoming drug resistance or apoptosis resistance and treating a malignancy in a subject. The method comprises (a) providing an intact minicell that contains a functional nucleic acid molecule or a plasmid comprising a segment that encodes a functional nucleic acid molecule, where the functional nucleic acid molecule targets the transcript of a protein that promotes drug resistance (b) bringing the minicell into contact with a target mammalian cell, such that the mammalian cell engulfs the minicell, and (c) delivering a chemotherapeutic drug to the target mammalian cell. Preferably, step (c) is performed after steps (a) and (b), to allow the functional nucleic acid to diminish resistance to the drug prior to the drug's administration. The drug may be delivered by any conventional means, but it preferably is delivered via an intact minicell.

In certain embodiments of the invention, the minicell is brought into contact with the target mammalian cell via a bispecific ligand. The bispecific ligand has specificity for both a surface component on the minicell and a surface component on the mammalian cell, such as a receptor. As a result, the ligand causes the minicell to bind to the mammalian cell, the minicell is engulfed by the mammalian cell, and the minicell payload is released into the cytoplasm of the mammalian cell. In other embodiments of the invention, the minicell is brought into contact with a target mammalian cell that is phagocytosis- or endocytosis-competent. The use of bispecific ligands is optional when a target cell is phagocytosis-competent.

In another aspect, the invention provides a composition comprising (i), intact minicells and (ii) a pharmaceutically acceptable carrier therefor, where the minicells contain a functional nucleic acid molecule or a plasmid that encodes a functional nucleic acid molecule. The functional nucleic acid molecule may be an shRNA or miRNA or other siRNA molecule, an antisense molecule, or a ribozyme molecule.

Preferably, the functional nucleic acid molecule targets the gene or transcript of a protein that promotes drug resistance, inhibits apoptosis, or contributes to a neoplastic phenotype. Particularly useful targets that contribute to drug resistance include ATP binding cassette transporters such as P-glycoprotein, MDR-2 and MDR-3. Particularly useful targets that contribute to apoptosis resistance include Bcl-2 (B cell leukemia/lymphoma), Bcl-$X_L$, A1/Bfl 1, focal adhesion kinase and p53 mutant protein. Other useful targets are oncogenic proteins and mutant tumor suppressor proteins. The plasmid may contain a regulatory element, such as a promoter, a terminator, an enhancer or a signal sequence that is operably linked to the segment that encodes a functional nucleic acid molecule. Further, the plasmid may contain a reporter element. The functional nucleic acid molecule may comprise multiple RNA interference sequences as miRNA or shRNA and these may be co-cistronic or expressed from separate promoters to enable simultaneous knockdown of multiple targets associated with drug resistance. In preferred embodiments, the composition contains fewer than one contaminating parent cell per $10^7$, $10^8$, $10^9$, $10^{10}$, $10^{11}$ or $10^{12}$ minicells.

In still another aspect, the invention provides for a use of intact minicells in the preparation of a medicament for use in a method of overcoming drug resistance or promoting apoptosis by administration of the medicament to a cell, tissue or organ. In the medicament, minicells contain a functional nucleic acid molecule or a plasmid encoding a functional nucleic acid molecule, where the functional nucleic acid molecule targets the transcript of a protein that promotes drug resistance or inhibits apoptosis. The disease treated in this context may be a cancer, for example, or an acquired disease, such as AIDS and tuberculosis.

The invention affords significant improvements over conventional methods and formulations for delivering functional nucleic acids in the context of cancer and HIV by (i) providing safe and stable vehicles for delivering functional nucleic acids, (ii) countering the principal mechanisms of drug resistance in diseased cells, (iii) reducing toxic side-effects associated with overcoming drug resistance, and (iv) providing targeted and drug-packaged vehicles to treat the disease.

DETAILED DESCRIPTION OF THE PREFERRED EMBODIMENTS

Figure 1:
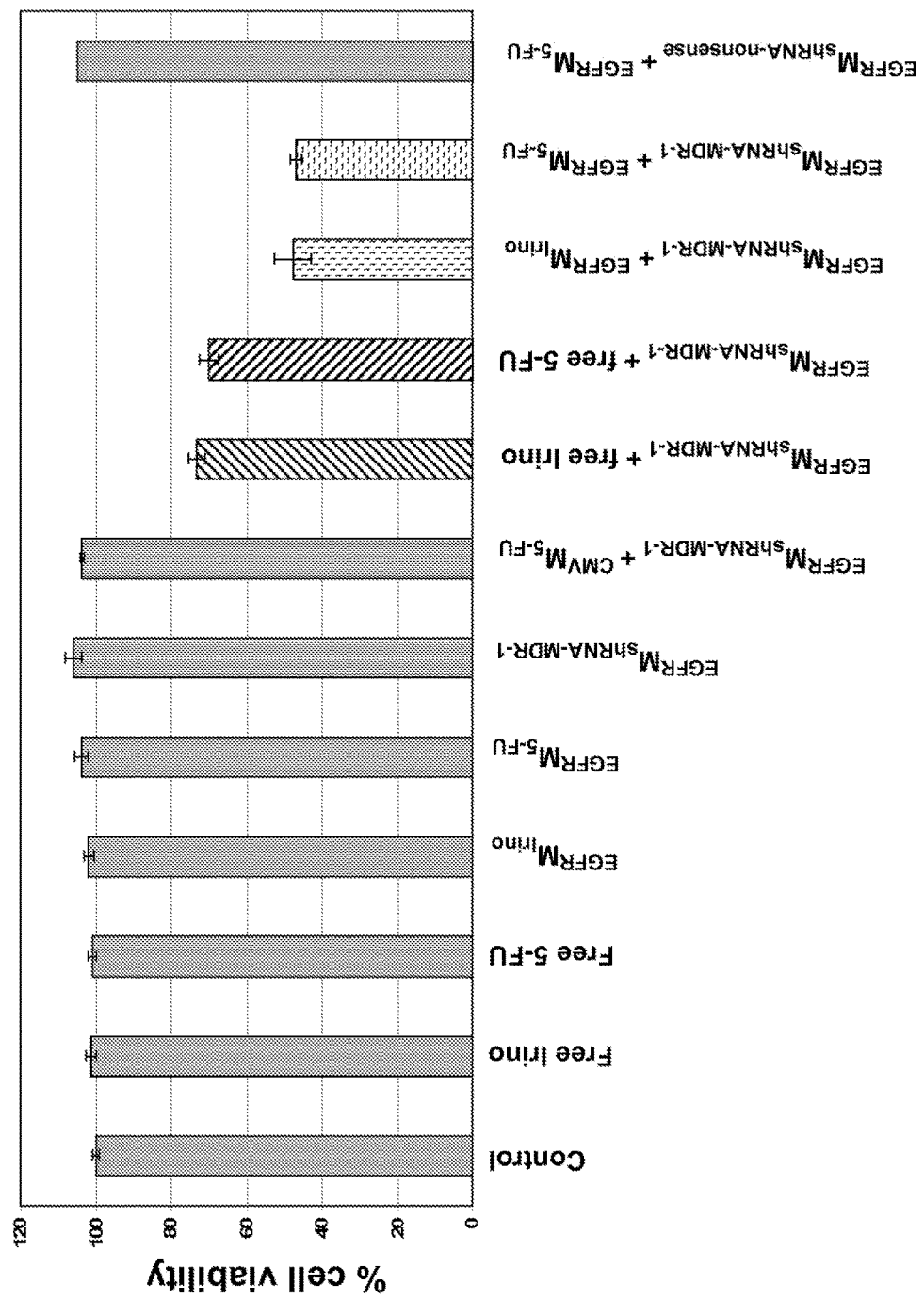
FIG. 1 shows the effect of various treatments on the viability of human colon cancer cell line Caco-2. The treatments are shown on the x-axis (minicells are designated by "M") and percent cell viability is shown by the bars. Each bar is a mean of six independent measurements and standard deviation of the mean is shown.

The inventors have discovered that intact bacterially derived minicells can safely and effectively introduce into target mammalian cells any of a range of functional nucleic acids, such as an siRNA molecule, a miRNA molecule, a ribozyme, or an antisense nucleic acid. In the particular context of cancer and HIV infection, the inventors have found that the introduction of functional nucleic acids into target cells, via intact minicells, can diminish drug resistance or apoptosis resistance in the target cells.

The inventors also have discovered that minicells can sequentially transfect the same target mammalian cells, particularly in vivo, and that minicells can sequentially deliver a range of different payloads to the same target mammalian cells. These discoveries are the first for any macroparticulate delivery vehicle and provide, for the first time, a method to treat complex multifactorial diseases like cancer and HIV where different therapeutic payloads need to be delivered to the same cell before a therapeutic effect is achieved. Similarly, the inventors have discovered that the complex problem of drug resistance associated with multiple mutations in different genes can be addressed with minicells that introduce multiple RNAi sequences into a host cell to counteract the multitude of genetic defects, and that following minicell-mediated RNAi delivery and allowing sufficient time for knockdown of target drug resistance-mediating proteins, cancer cells formerly resistant to specific chemotherapeutic drugs can effectively be treated with minicells packaged with the same drugs. This is the first in vivo demonstration of effectively treating cancer that is refractory to all other methods of treatment. The concentration of chemotherapeutic drugs, delivered via minicells, required to treat drug-resistant cancer cells effectively is discovered to be over 1000-fold less than free drug treatment. This is a surprising discovery because all previous methods to reverse drug resistance using RNAi or inhibitors of drug resistance-mediating proteins still required drug concentrations that can cause severe toxicity to a mammalian subject. Thus, methods of the invention, i.e., minicell-mediated delivery of RNAi followed by minicell-mediated chemotherapeutic drug, has the potential to treat cancer effectively without severe toxicity.

Additionally, the inventors have discovered that the serotype of minicells can be adapted to overcome a host immune response against minicells.

The following description outlines the invention related to these discoveries, without limiting the invention to the particular embodiments, methodology, protocols, or reagents described. Likewise, the terminology used here describes particular embodiments only and does not limit the scope of the invention.

I. Definitions

Unless defined otherwise, all technical and scientific terms used in this description have the same meaning as commonly understood by those skilled in the relevant art.

For convenience, the meaning of certain terms and phrases employed in the specification, examples, and appended claims are provided below. Other terms and phrases are defined throughout the specification.

The singular forms "a," "an," and "the" include plural reference unless the context clearly dictates otherwise.

"Antisense oligonucleotide" refers to a nucleic acid molecule complementary to a portion of a particular gene transcript that can hybridize to the transcript and block its translation. An antisense oligonucleotide may comprise RNA or DNA.

"Biomolecular sequence" or "sequence" refers to all or a portion of a polynucleotide or polypeptide sequence.

"Cancer," "neoplasm," "tumor," "malignancy" and "carcinoma," used interchangeably herein, refer to cells or tissues that exhibit an aberrant growth phenotype characterized by a significant loss of control of cell proliferation. The methods and compositions of this invention particularly apply to precancerous, malignant, pre-metastatic, metastatic, and non-metastatic cells.

"Complementary" refers to the topological compatibility or matching together of the interacting surfaces of two molecules, such as a functional nucleic acid molecule and its target. The molecules can be described as complementary, and furthermore, the contact surface characteristics are complementary to each other.

"Corresponds to" or "represents" when used in the context of, for example, a polynucleotide or sequence that "corresponds to" or "represents" a gene means that a sequence of the polynucleotide is present in the gene or in the nucleic acid gene product, e.g., mRNA. The polynucleotide may be wholly present within an exon of a genomic sequence of the gene, or different portions of the sequence of the polynucleotide may be present in different exons, e.g., such that the contiguous polynucleotide sequence is present in an mRNA, either pre- or post-splicing, that is an expression product of the gene.

"Cytokine" is a generic term for proteins released by one cell population that act on another cell population as intercellular mediators.

"Drug" refers to any physiologically or pharmacologically active substance that produces a local or systemic effect in animals, particularly mammals and humans.

"Expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein.

"Functional nucleic acid" refers to a nucleic acid molecule that, upon introduction into a host cell, specifically interferes with expression of a protein. In general, functional nucleic acid molecules have the capacity to reduce expression of a protein by directly interacting with a transcript that encodes the protein. Ribozymes, antisense nucleic acids and siRNA molecules, including shRNA molecules, short RNAs (typically less than 400 bases in length), micro-RNAs (miR-NAs) constitute exemplary functional nucleic acids.

"Gene" refers to a polynucleotide sequence that comprises control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

"Host cell" refers to a cell that may be, or has been, used as a recipient for a recombinant vector or other transfer of polynucleotides, and includes the progeny of the original cell that has been transfected. The progeny of a single cell may not necessarily be completely identical in morphology or in genomic or total DNA complement as the original parent due to natural, accidental, or deliberate mutation.

"Hybridization" refers to any process by which a polynucleotide sequence binds to a complementary sequence through base pairing.

"Individual," "subject," "host," and "patient," used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like. The invention also contemplates the use of radioactive isotopes, such as $^{35}S$, $^{32}P$, $^{3}H$, and the like as labels. Colorimetric labels such as colloidal gold or colored glass or plastic (e.g., polystyrene, polypropylene, latex) beads may also be utilized. For instance, see U.S. Pat. Nos. 4,366,241, 4,277,437, 4,275,149, 3,996,345, 3,939,350, 3,850,752, and U.S. Pat. No. 3,817,837.

"Oligonucleotide" refers to a polynucleotide comprising, for example, from about 10 nucleotides (nt) to about 1000 nt. Oligonucleotides for use in the invention are preferably from about 10 nt to about 150 nt. The oligonucleotide may be a naturally occurring oligonucleotide or a synthetic oligonucleotide. Oligonucleotides may be modified.

"Minicell" refers to anucleate forms of bacterial cells, engendered by a disturbance in the coordination, during binary fission, of cell division with DNA segregation. Minicells are distinct from other small vesicles that are generated and released spontaneously in certain situations and, in contrast to minicells, are not due to specific genetic rearrangements or episomal gene expression. For practicing the present invention, it is desirable for minicells to have intact cell walls ("intact minicells").

"Modified oligonucleotide" and "Modified polynucleotide" refer to oligonucleotides or polynucleotides with one or more chemical modifications at the molecular level of the natural molecular structures of all or any of the bases, sugar moieties, internucleoside phosphate linkages, as well as to molecules having added substitutions or a combination of modifications at these sites. The internucleoside phosphate linkages may be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5' linkages, and combinations of such similar linkages. The phosphodiester linkage may be replaced with a substitute linkage, such as phosphorothioate, methylamino, methylphosphonate, phosphoramidate, and guanidine, and the ribose subunit of the polynucleotides may also be substituted (e.g., hexose phosphodiester; peptide nucleic acids). The modifications may be internal (single or repeated) or at the end(s) of the oligonucleotide molecule, and may include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e.g., 3'-substituted ribonucleotides or deoxyribonucleotide monomers), any of which are bound together via 5' to 3' linkages.

The phrase "nucleic acid molecules" and the term "polynucleotides" denote polymeric forms of nucleotides of any length, either ribonucleotides or deoxynucleotides. They include single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. The backbone of a polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluororibose and thioate, and nucleotide branches. A polynucleotide may be further modified, such as by conjugation with a labeling component. Other types of modifications include caps, substitution of one or more of the naturally occurring nucleotides with an analog, and introduction of means for attaching the polynucleotide to proteins, metal ions, labeling components, other polynucleotides, or a solid support.

"Pharmaceutically acceptable" refers to physiological compatibility. A pharmaceutically acceptable carrier or excipient does not abrogate biological activity of the composition being administered, is chemically inert and is not toxic to the organism in which it is administered.

"Polypeptide" and "protein," used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

"Purified" refers to a compound that is removed from its natural environment and is at least about 60%, 65%, 70%, 75%, 80%, 85%, 90%, 91%, 92%, 93%, 94%, 95%, 96%, 97%, 98%, 99%, 99.9%, or 99.99% free from other components with which it is naturally associated.

"Ribozyme" refers to an RNA molecule having an enzymatic activity that can repeatedly cleave other RNA molecules in a nucleotide base sequence-specific manner.

"RNA interference" (RNAi) refers to sequence-specific or gene specific suppression of gene expression (protein synthesis) that is mediated by short interfering RNA (siRNA), short-haripin RNA, short RNA or micro-RNA.

"Sequence Identity" refers to a degree of similarity or complementarity. There may be partial identity or complete identity. A partially complementary sequence is one that at least partially inhibits an identical sequence from hybridizing to a target polynucleotide; it is referred to using the functional term "substantially identical." The inhibition of hybridization of the completely complementary sequence to the target sequence may be examined using a hybridization assay (Southern or Northern blot, solution hybridization, and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

Another way of viewing sequence identity, in the context to two nucleic acid or polypeptide sequences, entails referencing residues in the two sequences that are the same when aligned for maximum correspondence over a specified region. As used here, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Short interfering RNA" (siRNA) refers to double-stranded RNA molecules, generally, from about 10 to about 30 nucleotides long that are capable of mediating RNA interference (RNAi). As used herein, the term siRNA includes short hairpin RNAs, also known as shRNAs.

The terms "treatment," "treating," "treat," and the like refer to obtaining a desired pharmacological and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

II. Delivery of Functional Nucleic Acids via Minicells

In one aspect, the invention provides a method of delivering a functional nucleic acid to a target cell, comprising (a)

providing an intact minicell that contains a functional nucleic acid molecule or a plasmid comprising a segment that encodes a functional nucleic acid molecule, then, (b) bringing the minicell into contact with a target mammalian cell, such that the mammalian cell engulfs the minicell. Following engulfment of the minicell, the functional nucleic acid molecule is released into the cytoplasm of the target cell or expressed by the target cell. Minicells may be brought into contact with the target mammalian cells via bispecific ligands, as described in WO 2005/056749. Contact between the minicell and the target mammalian cell may be in vitro or in vivo.

A. Minicells

Minicells of the invention are anucleate forms of *E. coli* or other bacterial cells, engendered by a disturbance in the coordination, during binary fission, of cell division with DNA segregation. Prokaryotic chromosomal replication is linked to normal binary fission, which involves mid-cell septum formation. In *E. coli*, for example, mutation of min genes, such as minCD, can remove the inhibition of septum formation at the cell poles during cell division, resulting in production of a normal daughter cell and an anucleate minicell. See de Boer et al., 1992; Raskin & de Boer, 1999; Hu & Lutkenhaus, 1999; Harry, 2001. Minicells are distinct from other small vesicles that are generated and released spontaneously in certain situations and, in contrast to minicells, are not due to specific genetic rearrangements or episomal gene expression. For practicing the present invention, it is desirable for minicells to have intact cell walls ("intact minicells").

In addition to min operon mutations, anucleate minicells also are generated following a range of other genetic rearrangements or mutations that affect septum formation, for example in the divIVB1 in *B. subtilis*. See Reeve and Cornett, 1975; Levin et al., 1992. Minicells also can be formed following a perturbation in the levels of gene expression of proteins involved in cell division/chromosome segregation. For example, overexpression of minE leads to polar division and production of minicells. Similarly, chromosome-less minicells may result from defects in chromosome segregation for example the smc mutation in *Bacillus subtilis* (Britton et al., 1998), spoOJ deletion in *B. subtilis* (Ireton et al., 1994), mukB mutation in *E. coli* (Hiraga et al., 1989), and parC mutation in *E. coli* (Stewart and D'Ari, 1992). Gene products may be supplied in trans. When over-expressed from a high-copy number plasmid, for example, CafA may enhance the rate of cell division and/or inhibit chromosome partitioning after replication (Okada et al., 1994), resulting in formation of chained cells and anucleate minicells (Wachi et al., 1989; Okada et al., 1993). Minicells can be prepared from any bacterial cell of Gram-positive or Gram-negative origin.

In accordance with the invention, minicells contain a functional nucleic acid or a plasmid that encodes a functional nucleic acid for which delivery is desired. "Functional" nucleic acid molecules of the invention have the capacity to reduce expression of a protein by directly interacting with a transcript that encodes the protein. siRNA molecules, ribozymes, and antisense nucleic acids constitute exemplary functional nucleic acids.

B. siRNA Molecules

Short interfering RNA (siRNA) molecules are useful for performing RNA interference (RNAi), a post-transcriptional gene silencing mechanism. siRNA generally refers to double-stranded RNA molecules from about 10 to about 30 nucleotides long that are named for their ability specifically to interfere with protein expression. Preferably, siRNA molecules are 12-28 nucleotides long, more preferably 15-25 nucleotides long, still more preferably 19-23 nucleotides long and most preferably 21-23 nucleotides long. Therefore, preferred siRNA molecules are 12, 13, 14, 15, 16, 17, 18, 19, 20, 21, 22, 23, 24, 25, 26, 27 28 or 29 nucleotides in length.

The length of one strand designates the length of an siRNA molecule. For instance, an siRNA that is described as 21 ribonucleotides long (a 21-mer) could comprise two opposite strands of RNA that anneal together for 19 contiguous base pairings. The two remaining ribonucleotides on each strand would form an "overhang." When an siRNA contains two strands of different lengths, the longer of the strands designates the length of the siRNA. For instance, a dsRNA containing one strand that is 21 nucleotides long and a second strand that is 20 nucleotides long, constitutes a 21-mer.

siRNAs that comprise an overhang are desirable. The overhang may be at the 5' or the 3' end of a strand. Preferably, it is at the 3' end of the RNA strand. The length of an overhang may vary, but preferably is about 1 to about 5 bases, and more preferably is about 2 nucleotides long. Preferably, the siRNA of the present invention will comprise a 3' overhang of about 2 to 4 bases. More preferably, the 3' overhang is 2 ribonucleotides long. Even more preferably, the 2 ribonucleotides comprising the 3' overhang are uridine (U).

According to the invention, the term siRNA includes short hairpin RNAs (shRNAs). shRNAs comprise a single strand of RNA that forms a stem-loop structure, where the stem consists of the complementary sense and antisense strands that comprise a double-stranded siRNA, and the loop is a linker of varying size. The stem structure of shRNAs generally is from about 10 to about 30 nucleotides long. Preferably, the stem of shRNA molecules are 12-28 nucleotides long, more preferably 15-25 nucleotides long, still more preferably 19-23 nucleotides long and most preferably 21-23 nucleotides long. Therefore, preferred shRNA molecules comprise stems that are 12, 13, 14, 15, 16, 17, 18, 19, 20, 21, 22, 23, 24, 25, 26, 27 28 or 29 nucleotides in length.

siRNAs of the invention are designed to interact with a target ribonucleotide sequence, meaning they complement a target sequence sufficiently to hybridize to the target sequence. In one embodiment, the invention provides an siRNA molecule comprising a ribonucleotide sequence at least 70%, 75%, 80%, 85% or 90% identical to a target ribonucleotide sequence or the complement of a target ribonucleotide sequence. Preferably, the siRNA molecule is at least 90%, 95%, 96%, 97%, 98%, 99% or 100% identical to the target ribonucleotide sequence or the complement of the target ribonucleotide sequence. Most preferably, an siRNA will be 100% identical to the target nucleotide sequence or the complement of the ribonucleotide sequence. However, siRNA molecules with insertions, deletions or single point mutations relative to a target may also be effective.

Tools to assist siRNA design are readily available to the public. For example, a computer-based siRNA design tool is available on the internet at www.dharmacon.com.

C. Ribozymes

Ribozymes are RNA molecules having an enzymatic activity that can repeatedly cleave other RNA molecules in a nucleotide base sequence-specific manner. Such enzymatic RNA molecules may be targeted to virtually any RNA transcript, and efficient cleavage achieved in vitro.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic polynucleotides act by first binding to a target RNA. Such binding occurs through the target binding portion of a enzymatic polynucleotide which is held in close proximity to an enzymatic portion of the molecule that acts to cleave the target RNA. Thus, the enzymatic polynucleotide first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic polynucleotide has bound and cleaved its RNA target, it is released from that RNA to search for another target and can repeatedly bind and cleave new targets.

The enzymatic nature of a ribozyme is advantageous. Because a single ribozyme molecule is able to cleave many molecules of target RNA, effective concentrations of ribozyme can be quite low.

Useful ribozymes may comprise one of several motifs, including hammerhead (Rossi et al. (1992)), hairpin (Hampel and Tritz, (1989), Hampel et al. (1990)), hepatitis delta virus motif (Perrotta and Been (1992), group I intron (U.S. Pat. No. 4,987,071), RNaseP RNA in association with an RNA guide sequence (Guerrier-Takada et al. (1983)), and Neurospora VS RNA (Saville & Collins (1990); Saville & Collins (1991); Collins & Olive (1993)). These specific motifs are not limiting, as all that is important in a ribozyme of this invention is that it has a specific substrate binding site that is complementary to one or more target RNA regions, and that it have nucleotide sequences within or surrounding that substrate binding site which impart an RNA cleaving activity to the molecule.

Ribozymes of the invention may comprise modified oligonucleotides (e.g., for improved stability, targeting, etc.). Nucleic acid sequences encoding the ribozymes may be under the control of a strong constitutive promoter, such as, for example, RNA Polymerase II or RNA Polymerase III promoter, so that transfected cells will produce sufficient quantities of the ribozyme to destroy target endogenous messages and inhibit translation.

D. Antisense Oligonucleotides

Antisense oligonucleotides of the invention specifically hybridize with a nucleic acid encoding a protein, and interfere with transcription or translation of the protein. In one embodiment, an antisense oligonucleotide targets DNA and interferes with its replication and/or transcription. In another embodiment, an antisense oligonucleotide specifically hybridizes with RNA, including pre-mRNA and mRNA. Such antisense oligonucleotides may affect, for example, translocation of the RNA to the site of protein translation, translation of protein from the RNA, splicing of the RNA to yield one or more mRNA species, and catalytic activity that may be engaged in or facilitated by the RNA. The overall effect of such interference is to modulate, decrease, or inhibit target protein expression.

There are several sites within a gene that may be utilized in designing an antisense oligonucleotide. For example, an antisense oligonucleotide may bind the region encompassing the translation initiation codon, also known as the start codon, of the open reading frame. In this regard, "start codon and "translation initiation codon" generally refer to the portion of such mRNA or gene that encompasses from at least about 25 to at least about 50 contiguous nucleotides in either direction (i.e., 5' or 3') from a translation initiation codon.

Another site for antisense interaction to occur is the termination codon of the open reading frame. The terms "stop codon region" and "translation termination codon region" refer generally to a portion of such a mRNA or gene that encompasses from at least about 25 to at least about 50 contiguous nucleotides in either direction form a translation termination codon.

The open reading frame or coding region also may be targeted effectively. The open reading frame is generally understood to refer to the region between the translation initiation codon and the translation termination codon. Another target region is the 5' untranslated region, which is the portion of a mRNA in the 5' direction from the translation initiation codon. It includes the nucleotides between the 5' cap site and the translation initiation codon of a mRNA or corresponding nucleotides on the gene.

Similarly, the 3' untranslated region may be used as a target for antisense oligonucleotides. The 3' untranslated region is that portion of the mRNA in the 3' direction from the translation termination codon, and thus includes the nucleotides between the translation termination codon and the 3' end of a mRNA or corresponding nucleotides of the gene.

An antisense oligonucleotide may also target the 5' cap region of an mRNA. The 5' cap comprises an N7-methylated guanosine residue joined to the 5'-most residue of the mRNA via 5'-5' triphosphate linkage. The 5' cap region is considered to include the 5' cap structure itself as well as the first 50 nucleotides adjacent to the cap.

Although some eukaryotic mRNA transcripts are directly translated, many contain one or more intron regions, which are excised from a transcript before it is translated. The remaining (and therefore translated) exon regions are spliced together to form a continuous mRNA sequence. mRNA splice sites, i.e., intron-exon junctions, represent possible target regions, and are particularly useful in situations where aberrant splicing is implicated in disease, or where an overproduction of a particular mRNA splice product is implicated in disease. Moreover, aberrant fusion junctions due to rearrangements or deletions are also possible targets for antisense oligonucleotides.

With these various target sites in mind, antisense oligonucleotides that are sufficiently complementary to the target polynucleotides must be chosen. There must be a sufficient degree of complementarity or precise pairing such that stable and specific binding occurs between the oligonucleotide and the polynucleotide target. Importantly, the sequence of an antisense oligonucleotide need not be 100% complementary to that of its target polynucleotide to be specifically hybridizable. An antisense oligonucleotide is specifically hybridizable when binding of the antisense oligonucleotide to the target polynucleotide interferes with the normal function of the target polynucleotide to cause a loss of utility, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

The antisense oligonucleotides may be at least about 8 nt to at least about 50 nt in length. In one embodiment, the antisense oligonucleotides may be about 12 to about 30 nt in length.

The antisense oligonucleotides used in accordance with this invention may be conveniently and routinely made through the well-known technique of solid phase synthesis.

Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

E. Nucleic Acids Encoding Functional Nucleic Acids

In preferred embodiments of the invention, minicells comprise nucleic acids that encode functional nucleic acids. For example, a plasmid may encode a functional nucleic acid that is expressed inside of mammalian target cells. This makes possible endogenous delivery of functional nucleic acids, which has advantages over the transient nature of exogenous delivery.

Thus, recombinant intact minicells may carry plasmid DNA encoding one or more siRNA sequences aimed at silencing drug resistance or apoptosis resistance genes. Using minicells that encode multiple functional nucleic acids, it is possible to treat cells that express multiple drug resistance mechanisms. Different siRNA sequences can be expressed individually from different promoters. For example, siRNA targeting Pgp mRNA can be expressed from the U6 promoter and siRNA targeting Bcl-2 mRNA can be expressed from the H1 promoter. These multiple expression cassettes preferably are carried on a single plasmid, but may also be on different plasmids. Different siRNA sequences also can be expressed from a single promoter, where the recombinant plasmid carries an expression cassette comprised of multiple siRNA-encoding sequences, which are linked together via non-coding polynucleotide sequences. A single gene transcription terminator can be placed downstream of the complete expression cassette.

In one strategy, a plasmid encodes the sense and antisense strands of an siRNA as two independent transcripts that, after expression within a target cell, hybridize to form functional siRNA duplexes. In a second preferred strategy, a plasmid encodes one or more siRNAs that each are expressed as a single transcript that forms a short hairpin RNA stem-loop structure. The hairpin structure may be processed by a Dicer enzyme into functional siRNA.

F. Reporter Elements

A nucleic acid molecule to be introduced via the approach of the present invention can include a reporter element. A reporter element confers on its recombinant host a readily detectable phenotype or characteristic, typically by encoding a polypeptide, not otherwise produced by the host, that can be detected, upon expression, by histological or in situ analysis, such as by in vivo imaging techniques. For example, a reporter element delivered by an intact minicell, according to the present invention, could code for a protein that produces, in the engulfing host cell, a colorimetric or fluorometric change that is detectable by in situ analysis and that is a quantitative or semi-quantitative function of transcriptional activation. Illustrative of these proteins are esterases, phosphatases, proteases and other enzymes, the activity of which generates a detectable chromophore or fluorophore.

Preferred examples are E. coli β-galactosidase, which effects a color change via cleavage of an indigogenic substrate, indolyl-β-D-galactoside, and a luciferase, which oxidizes a long-chain aldehyde (bacterial luciferase) or a heterocyclic carboxylic acid (luciferin), with the concomitant release of light. Also useful in this context is a reporter element that encodes the green fluorescent protein (GFP) of the jellyfish, Aequorea victoria, as described by Prasher et al. (1995). The field of GFP-related technology is illustrated by two published PCT applications, WO 095/21191 (discloses a polynucleotide sequence encoding a 238 amino-acid GFP apoprotein, containing a chromophore formed from amino acids 65 through 67) and WO 095/21191 (discloses a modification of the cDNA for the apopeptide of A. victoria GFP, providing a peptide having altered fluorescent properties), and by a report of Heim et al. (1994) of a mutant GFP, characterized by a 4-to-6-fold improvement in excitation amplitude.

Another type of a reporter element is associated with an expression product that renders the recombinant minicell resistant to a toxin. For instance, the neo gene protects a host against toxic levels of the antibiotic G418, while a gene encoding dihydrofolate reductase confers resistance to methotrexate, and the chloramphenicol acetyltransferase (CAT) gene bestows resistance to chloramphenicol.

Other genes for use as a reporter element include those that can transform a host minicell to express distinguishing cell-surface antigens, e.g., viral envelope proteins such as HIV gp120 or herpes gD, which are readily detectable by immunoassays.

G. Regulatory Elements

A nucleic acid molecule to be introduced via the approach of the present invention also can have a desired encoding segment linked operatively to a regulatory element, such as a promoter, a terminator, an enhancer and/or a signal sequence. A suitable promoter can be tissue-specific or even tumor-specific, as the therapeutic context dictates.

A promoter is "tissue-specific" when it is activated preferentially in a given tissue and, hence, is effective in driving expression, in the target tissue, of an operably linked structural sequence. The category of tissue-specific promoters includes, for example: the hepatocyte-specific promoter for albumin and $a_1$-antitrypsin, respectively; the elastase I gene control region, which is active in pancreatic acinar cells; the insulin gene control region, active in pancreatic beta cells; the mouse mammary tumor virus control region, which is active in testicular, breast, lymphoid and mast cells; the myelin basic protein gene control region, active in oligodendrocyte cells in the brain; and the gonadotropic releasing hormone gene control region, which is active in cells of the hypothalamus. See Frain et al. (1990), Ciliberto et al. (1985), Pinkert et al., (1987), Kelsey et al. (1987), Swift et al. (1984), MacDonald (1987), Hanahan, (1985), Leder et al. (1986), Readhead et al. (1987), and Mason et al. (1986).

There also are promoters that are expressed preferentially in certain tumor cells or in tumor cells per se, and that are useful for treating different cancers in accordance with the present invention. The class of promoters that are specific for cancer cells is illustrated by: the tyrosinase promoter, to target melanomas; the MUC1/Df3 promoter, to target breast carcinoma; the hybrid myoD enhancer/SV40 promoter, which targets expression to rhabdomyosarcoma (RMS); the carcinoembryonic antigen (CEA) promoter, which is specific for CEA-expressing cells such as colon cancer cells, and the hexokinase type II gene promoter, to target non-small cell lung carcinomas. See Hart (1996), Morton & Potter (1998), Kurane et al. (1998) and Katabi et al. (1999).

Promoters that are dependent on either RNA polymerase (pol) II or pol II are preferred promoters. Highly preferred promoters are the RNA III polymerase promoters H1 and U6.

A signal sequence can be used, according to the present invention, to effect secretion of an expression product or localization of an expression product to a particular cellular compartment. Thus, a therapeutic polynucleotide molecule that is delivered via intact minicells may include a signal sequence, in proper reading frame, such that the expression product of interest is secreted by an engulfing cell or its progeny, thereby to influence surrounding cells, in keeping with the chosen treatment paradigm. Illustrative signal sequences include the haemolysin C-terminal secretion sequence, described in U.S. Pat. No. 5,143,830, the BAR1 secretion sequence, disclosed in U.S. Pat. No. 5,037,743, and the signal sequence portion of the zsig32 polypeptide, described in U.S. Pat. No. 6,025,197.

H. Targets of Functional Nucleic Acids

Functional nucleic acids of the invention target the gene or transcript of a protein that promotes drug resistance, inhibits apoptosis or promotes a neoplastic phenotype. Successful application of functional nucleic acid strategies in these contexts have been achieved in the art, but without the benefits of minicell vectors. See, e.g., Sioud (2004), Caplen (2003), Wu et al. (2003), Nieth et al. (2003), Caplen and Mousses (2003), Duxbury et al. (2004), Yague et al. (2004), Duan et al. (2004), Proteins that contribute to drug resistance constitute preferred targets of functional nucleic acids. The proteins may contribute to acquired drug resistance or intrinsic drug resistance. When diseased cells, such as tumor cells, initially respond to drugs, but become refractory on subsequent treatment cycles, the resistant phenotype is acquired. Useful targets involved in acquired drug resistance include ATP binding cassette transporters such as P-glycoprotein (P-gp, P-170, PGY1, MDR1, ABCB1, MDR-associated protein, Multidrug resistance protein 1), MDR-2 and MDR-3. MRP2 (multi-drug resistance associated protein), BCR-ABL (breakpoint cluster region-Abelson protooncogene), a STI-571 resistance-associated protein, lung resistance-related protein, cyclooxygenase-2, nuclear factor kappa, XRCC1 (X-ray cross-complementing group 1), ERCC1 (Excision cross-complementing gene), GSTP1 (Glutathione S-transferase), mutant β-tubulin, and growth factors such as IL-6 are additional targets involved in acquired drug resistance. When previously untreated cells fail to respond to one or more drugs, the resistant phenotype is intrinsic. An example of a protein contributing to intrinsic resistance is LRP (lung resistance-related protein).

Useful targets also include proteins that contribute to apoptosis resistance. These include Bcl-2 (B cell leukemia/lymphoma), Bcl-$X_L$, A1/Bfl 1, focal adhesion kinase and p53 mutant protein.

Useful targets further include oncogenic and mutant tumor suppressor proteins. Examples include β-Catenin, PKC-α (protein kinase C), C-RAF, K-Ras (V12), DP97 Dead box RNA helicase, DNMT1 (DNA methyltransferase 1), FLIP (Flice-like inhibitory protein), C-Sfc, 53BPI, Polycomb group protein EZH2 (Enhancer of zeste homologue), ErbB1, HPV-16 E5 and E7 (human papillomavirus early 5 and early 7), Fortilin & MCl1P (Myeloid cell leukemia 1 protein), DIP13α (DDC interacting protein 13a), MBD2 (Methyl CpG binding domain), p21, KLF4 (Kruppel-like factor 4), tpt/TCTP (Translational controlled tumor protein), SPK1 & SPK2 (Sphingosine kinase), P300, PLK1 (Polo-like kinase-1), Trp53, Ras, ErbB1, VEGF (Vascular endothelial growth factor), and BAG-1 (BCL2-associated athanogene 1).

With regard to HIV infection, targets include HIV-Tat, HIV-Rev, HIV-Vif, HIV-Nef, HIV-Gag, HIV-Env, LTR, CD4, CXCR4 (chemokine receptor) and CCRS (chemokine receptor).

Because of tumor cell heterogeneity, a number of different drug resistance or apoptosis resistance pathways may be operational in target cells. Therefore, the functional nucleic acids used in methods of the invention may require change over time. For instance, if biopsy samples reveal new mutations that result in acquired drug resistance, specific siRNAs can be designed and encoded on a suitable expression plasmid, which is transformed into a minicell-producing bacterial strain, which is used to produce recombinant minicells that are administered to address the acquired drug resistance.

III. Method of Overcoming Drug Resistance and Treating Disease

In another aspect, the invention provides a method of overcoming drug resistance and treating a disease, such as cancer or AIDS, in a subject. The method comprises (a) providing an intact minicell that contains a functional nucleic acid molecule or a plasmid comprising a segment that encodes a functional nucleic acid molecule, where the functional nucleic acid molecule targets the gene or transcript of a protein that promotes drug resistance, (b) bringing the minicell into contact with a target mammalian cell, such that the mammalian cell engulfs the minicell, and (c) delivering a drug to the target mammalian cell. Preferably, step (c) is performed after steps (a) and (b), to allow the functional nucleic acid to diminish resistance to the drug prior to the drug's administration. Delivery of the drug and introduction of the functional nucleic acid can occur consecutively, in any order, or simultaneously.

According to the invention, drugs may be delivered by any conventional means. For example, drugs may be delivered orally, parenterally (including subcutaneously, intravenously, intramuscularly, intraperitoneally, and by infusion), topically, transdermally or by inhalation. The appropriate mode of delivery and dosage of each drug is easily ascertainable by those skilled in the medical arts.

A. Drug Delivery via Minicells

Although drug delivery may occur via conventional means, delivery via minicells is preferred. In this regard, the inventors have discovered that the same mammalian cells can be successfully re-transfected by targeted intact minicells that are packaged with different payloads. For example, siRNA-encoding plasmid-packaged minicells can transfect a mammalian cell, after which drug-packaged minicells can deliver drug to the same mammalian cell. This discovery was a surprise, and indicates that the intracellular processes associated with minicell breakdown, endosomal release of a payload and escape of the payload to intracellular targets remains fully functional after the first round of transfection and payload delivery.

The drug may be packaged in a separate minicell from the functional nucleic acid or plasmid encoding the functional nucleic acid. Alternatively, the drug may be packaged in the same minicell as the functional nucleic acid molecule or plasmid encoding the functional nucleic acid molecule. Certain drugs may interact with nucleic acids and preclude co-packaging of drug and nucleic acid in the same minicell. For example, Doxorubicin is known to interact with DNA.

Preferably, minicells of the invention contain a sufficient quantity of drug to exert the drug's physiological or pharmacological effect on a target cell. Also preferably, drugs contained within the minicells are heterologous, or foreign, to the minicells, meaning that the minicells' parent bacterial cells do not normally produce the drug.

Both hydrophilic and hydrophobic drugs can be packaged in minicells by creating a concentration gradient of the drug between en extracellular medium containing minicells and the minicell cytoplasm. When the extracellular medium contains a higher drug concentration than the minicell cytoplasm, the drug naturally moves down this concentration gradient, into the minicell cytoplasm. When the concentration gradient is reversed, however, the drug does not move out of the minicells.

To load minicells with drugs that normally are not water soluble, the drugs initially can be dissolved in an appropriate solvent. For example, Paclitaxel can be dissolved in a 1:1 blend of ethanol and cremophore EL (polyethoxylated castor oil), followed by a dilution in PBS to achieve a solution of Paclitaxel that is partly diluted in aqueous media and carries minimal amounts of the organic solvent to ensure that the drug remains in solution. Minicells can be incubated in this final medium for drug loading. Thus, the inventors discovered that even hydrophobic drugs can diffuse into the cytoplasm of minicells to achieve a high and therapeutically significant cytoplasmic drug load. This is unexpected because the minicell membrane is composed of a hydrophobic phospholipid bilayer, which would be expected to prevent diffusion of hydrophobic molecules into the cytoplasm.

Another method of loading minicells with a drug involves culturing a recombinant parent bacterial cell under conditions wherein the parent bacterial cell transcribes and translates a nucleic acid encoding the drug, such that the drug is released into the cytoplasm of the parent bacterial cell. For example, a gene cluster encoding the cellular biosynthetic pathway for a desired drug can be cloned and transferred into a parent bacterial strain that is capable of producing minicells. Genetic transcription and translation of the gene cluster results in biosynthesis of the drug within the cytoplasm of the parent bacterial cells, filling the bacterial cytoplasm with the drug. When the parent bacterial cell divides and forms progeny minicells, the minicells also contain the drug in their cytoplasm. The pre-packaged minicells can be purified by any of the minicell purification processes known in the art and described above.

Similarly, another method of loading minicells with a drug involves culturing a recombinant minicell that contains an expression plasmid encoding the drug under conditions such that the gene encoding the drug is transcribed and translated within the minicell.

B. Drugs

Drugs useful in the invention may be any physiologically or pharmacologically active substance that produces a desired local or systemic effect in animals, particularly mammals and humans. Drugs may be inorganic or organic compounds, without limitation, including peptides, proteins, nucleic acids, and small molecules, any of which may be characterized or uncharacterized. They may be in various forms, such as unchanged molecules, molecular complexes, pharmacologically acceptable salts, such as hydrochloride, hydrobromide, sulfate, laurate, palmitate, phosphate, nitrite, nitrate, borate, acetate, maleate, tartrate, oleate, salicylate, and the like. For acidic drugs, salts of metals, amines or organic cations, for example, quaternary ammonium, can be used. Derivatives of drugs, such as bases, esters and amides also can be used. A drug that is water insoluble can be used in a form that is a water soluble derivative thereof, or as a base derivative thereof, which in either instance, or by its delivery, is converted by enzymes, hydrolyzed by the body pH, or by other metabolic processes to the original therapeutically active form.

Useful drugs include chemotherapeutic agents, immunosuppressive agents, cytokines, cytotoxic agents, nucleolytic compounds, radioactive isotopes, receptors, and pro-drug activating enzymes, which may be naturally occurring or produced by recombinant methods.

Drugs that are affected by classical multidrug resistance have particular utility in the invention, such as vinca alkaloids (e.g., vinblastine and vincristine), the anthracyclines (e.g., doxorubicin and daunorubicin), RNA transcription inhibitors (e.g., actinomycin-D) and microtubule stabilizing drugs (e.g., paclitaxel). (Ambudkar et al., 1999)

In general, cancer chemotherapy agents are preferred drugs. Useful cancer chemotherapy drugs include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, Melphalan, Mercaptopurine, Methotrexate, Mitomycin, Mitotane, Mitoxantrone, Oxaliplatin, Paclitaxel, Pamidronate, Pentostatin, Plicamycin, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Vinblastine, Vincristine, Vindesine, Vinorelbine, VP-16, and Xeloda.

Useful cancer chemotherapy drugs also include alkylating agents such as Thiotepa and cyclosphosphamide; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophaoramide and trimethylolomelamine; nitrogen mustards such as Chlorambucil, Chlornaphazine, Cholophosphamide, Estramustine, Ifosfamide, mechlorethamine, mechlorethamine oxide hydrochloride, Melphalan, Novembiehin, Phenesterine, Prednimustine, Trofosfamide, uracil mustard; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Carminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman; Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Chlorambucil; Gemcitabine; 6-thioguanine; Mercaptopurine; Methotrexate; platinum analogs such as Cisplatin And Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

Useful drugs also include cytokines. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and β; mullerian-inhibiting substance; mouse gonadotropin-associated peptide; inhibin; activin; vascular endothelial growth factor; integrin; thrombopoietin (TPO); nerve growth factors such as NGF-β; platelet growth factor; transforming growth factors (TGFs) such as TGF-α and TGF-β; insulin-like growth factor-I and -II; erythropoietin (EPO); osteoinductive factors; interferons such as interferon-α, -β and -γ; colony stimulating factors (CSFs) such as macrophage-CSF (M-CSF); granulocyte-macrophage-CSF (GM-CSF); and granulocyte-CSF (GCSF); interleukins (ILs) such as IL-1, IL-1a, IL-2, IL-3, IL-4, IL-5, IL-6, IL-7, IL-8, IL-9, IL-11, IL-12, IL-15; a tumor necrosis factor such as TNF-α or TNF-β; and other polypeptide factors including LIF and kit ligand (KL). As used herein, the tern cytokine includes proteins from natural sources or from recombinant cell culture and biologically active equivalents of the native sequence cytokines.

The drugs may be prodrugs, subsequently activated by a prodrug-activating enzyme that converts a prodrug like a peptidyl chemotherapeutic agent to an active anti-cancer drug. See, e.g., WO 88/07378; WO 81/01145; U.S. Pat. No. 4,975,278. In general, the enzyme component includes any enzyme capable of acting on a prodrug in such a way so as to covert it into its more active, cytotoxic form.

IV. Directing Minicells to Specific Mammalian Cells

In one aspect of the invention, a minicell is directed to a target mammalian cell via a bispecific ligand, as described in WO 2005/056749. The bispecific ligand, having specificity for both minicell and mammalian cell components, causes the minicell to bind to the mammalian cell, such that the minicell is engulfed by the mammalian cell, and the mammalian cell produces the functional nucleic acid molecule. This targeted delivery method may be performed in vivo or in vitro, or both in vivo and in vitro.

Contact between bispecific ligand, minicell and mammalian cell may occur in a number of different ways. For in vivo delivery, it is preferable to administer a minicell that already has the bispecific ligand attached to it. Thus, minicell, bispecific ligand and target cell all are brought into contact when the bispecific ligand-targeted minicell reaches the target cell in vivo. Alternatively, bispecific ligand and minicell can be separately administered in vivo.

Contact between the bispecific ligands, minicells and mammalian cells also may occur during one or more incubations in vitro. In one embodiment, the three elements are incubated together all at once. Alternatively, step-wise incubations may be performed. In one example of a step-wise approach, minicells and bi-specific ligands are first incubated together to form bispecific ligand-targeted minicells, which are then incubated with target cells. In another example, bispecific ligands are first incubated with target cells, followed by an incubation with minicells. A combination of one or more in vitro incubations and in vivo administrations also may bring bispecific ligands, minicells and mammalian target cells into contact.

The inventors found that the targeted delivery approach is broadly applicable to a range of mammalian cells, including cells that normally are refractory to specific adhesion and endocytosis of minicells. For example, bispecific antibody ligands with anti-O-polysaccharide specificity on one arm and anti-HER2 receptor, anti-EGF receptor or anti-androgen receptor specificity on the other arm efficiently bind minicells to the respective receptors on a range of target non-phagocytic cells. These cells include lung, ovarian, brain, breast, prostate and skin cancer cells. Moreover, the efficient binding precedes rapid endocytosis of the minicells by each of the non-phagocytic cells.

Target cells of the invention include any cell into which a functional nucleic acid is to be introduced. Desirable target cells are characterized by expression of a cell surface receptor that, upon binding of a ligand, facilitates endocytosis. Preferred target cells are non-phagocytic, meaning that the cells are not professional phagocytes, such as macrophages, dendritic cells and Natural Killer (NK) cells. Preferred target cells also are mammalian.

Ligands useful in the targeted delivery methods of this invention include any agent that binds to a surface component on a target cell and to a surface component on a minicell. Preferably, the surface component on a target cell is a receptor, especially a receptor capable of mediating endocytosis. The ligands may comprise a polypeptide and/or carbohydrate component. Antibodies are preferred ligands. For example, a bispecific antibody that carries dual specificities for a surface component on bacterially derived intact minicells and for a surface component on target mammalian cells, can be used efficiently to target the minicells to the target mammalian cells in vitro and in vivo. Useful ligands also include receptors, enzymes, binding peptides, fusion/chimeric proteins and small molecules.

The selection of a particular ligand is made on two primary criteria: (i) specific binding to one or more domains on the surface of intact minicells and (ii) specific binding to one or more domains on the surface of the target cells. Thus, ligands preferably have a first arm that carries specificity for a bacterially derived intact minicell surface structure and a second arm that carries specificity for a mammalian cell surface structure. Each of the first and second arms may be multivalent. Preferably, each arm is monospecific, even if multivalent.

For binding to bacterially derived minicells, it is desirable for one arm of the ligand to be specific for the O-polysaccharide component of a lipopolysaccharide found on the parent bacterial cell. Other minicell surface structures that can be exploited for ligand binding include cell surface-exposed polypeptides and carbohydrates on outer membranes, such as pilli, fimbrae and flagella cell surface exposed peptide segments.

For binding to target cells, one arm of the ligand is specific for a surface component of a mammalian cell. Such components include cell surface proteins, peptides and carbohydrates, whether characterized or uncharacterized. Cell surface receptors, especially those capable of activating receptor-mediated endocytosis, are desirable cell surface components for targeting. Such receptors, if over-expressed on the target cell surface, confer additional selectivity for targeting the cells to be treated, thereby reducing the possibility for delivery to non-target cells.

By way of example, one may target tumor cells, metastatic cells, vasculature cells, such as endothelial cells and smooth muscle cells, lung cells, kidney cells, blood cells, bone marrow cells, brain cells, liver cells, and so forth, or precursors of any selected cell by selecting a ligand that specifically binds a cell surface receptor motif on the desired cells. Examples of cell surface receptors include carcinoembryonic antigen (CEA), which is overexpressed in most colon, rectum, breast, lung, pancreas and gastrointestinal tract carcinomas (Marshall, 2003); heregulin receptors (HER-2, neu or c-erbB-2), which is frequently overexpressed in breast, ovarian, colon, lung, prostate and cervical cancers (Hung et al., 2000); epidermal growth factor receptor (EGFR), which is highly expressed in a range of solid tumors including those of the breast, head and neck, non-small cell lung and prostate (Salomon et al., 1995); asialoglycoprotein receptor (Stockert, 1995); transferrin receptor (Singh, 1999); serpin enzyme complex receptor, which is expressed on hepatocytes (Ziady et al., 1997); fibroblast growth factor receptor (FGFR), which is overexpressed on pancreatic ductal adenocarcinoma cells (Kleeff et al., 2002); vascular endothelial growth factor receptor (VEGFR), for anti-angiogenesis gene therapy (Becker et al., 2002 and Hoshida et al., 2002); folate receptor, which is selectively overexpressed in 90% of nonmucinous ovarian carcinomas (Gosselin and Lee, 2002); cell surface glycocalyx (Batra et al., 1994); carbohydrate receptors (Thurnher et al., 1994); and polymeric immunoglobulin receptor, which is useful for gene delivery to respiratory epithelial cells and attractive for treatment of lung diseases such as Cystic Fibrosis (Kaetzel et al., 1997).

Preferred ligands comprise antibodies and/or antibody derivatives. As used herein, the term "antibody" encompasses an immunoglobulin molecule obtained by in vitro or in vivo generation of an immunogenic response. The term "antibody" includes polyclonal, monospecific and monoclonal antibodies, as well as antibody derivatives, such as single-chain antibody fragments (scFv). Antibodies and antibody derivatives useful in the present invention also may be obtained by recombinant DNA techniques.

Wild type antibodies have four polypeptide chains, two identical heavy chains and two identical light chains. Both types of polypeptide chains have constant regions, which do not vary or vary minimally among antibodies of the same class, and variable regions. Variable regions are unique to a particular antibody and comprise an antigen binding domain that recognizes a specific epitope. The regions of the antigen binding domain that are most directly involved in antibody binding are "complementarity-determining regions" (CDRs).

The term "antibody" also encompasses derivatives of antibodies, such as antibody fragments that retain the ability to specifically bind to antigens. Such antibody fragments include Fab fragments (a fragment that contains the antigen-binding domain and comprises a light chain and part of a heavy chain bridged by a disulfide bond), Fab' (an antibody fragment containing a single antigen-binding domain comprising a Fab and an additional portion of the heavy chain through the hinge region, F(ab')2 (two Fab' molecules joined by interchain disulfide bonds in the hinge regions of the heavy chains), a bispecific Fab (a Fab molecule having two antigen binding domains, each of which may be directed to a different epitope), and an scFv (the variable, antigen-binding determinative region of a single light and heavy chain of an antibody linked together by a chain of amino acids.)

When antibodies, including antibody fragments, constitute part or all of the ligands, they preferably are of human origin or are modified to be suitable for use in humans. So-called "humanized antibodies" are well known in the art. See, e.g., Osbourn et al., 2003. They have been modified by genetic manipulation and/or in vitro treatment to reduce their antigenicity in a human. Methods for humanizing antibodies are described, e.g., in U.S. Pat. No. 6,639,055, 5,585,089, and 5,530,101. In the simplest case, humanized antibodies are formed by grafting the antigen-binding loops, known as complementarity-determining regions (CDRs), from a mouse mAb into a human IgG. See Jones et al., 1986; Riechmann et al., 1988; and Verhoeyen et al., 1988. The generation of high-affinity humanized antibodies, however, generally requires the transfer of one or more additional residues from the so-called framework regions (FRs) of the mouse parent mAb. Several variants of the humanization technology also have been developed. See Vaughan et al., 1998.

Human antibodies, rather than "humanized antibodies," also may be employed in the invention. They have high affinity for their respective antigens and are routinely obtained from very large, single-chain variable fragments (scFvs) or Fab phage display libraries. See Griffiths et al., 1994; Vaughan et al., 1996; Sheets et al., 1998; de Haard et al., 1999; and Knappik et al., 2000.

Useful ligands also include bispecific single chain antibodies, which typically are recombinant polypeptides consisting of a variable light chain portion covalently attached through a linker molecule to a corresponding variable heavy chain portion. See U.S. Pat. Nos. 5,455,030, 5,260,203, and 4,496,778. Bispecific antibodies also can be made by other methods. For example, chemical heteroconjugates can be created by chemically linking intact antibodies or antibody fragments of different specificities. See Karpovsky et al., 1984. However, such heteroconjugates are difficult to make in a reproducible manner and are at least twice as large as normal monoclonal antibodies. Bispecific antibodies also can be created by disulfide exchange, which involves enzymatic cleavage and reassociation of the antibody fragments. See Glennie et al., 1987.

Because Fab and scFv fragments are monovalent they often have low affinity for target structures. Therefore, preferred ligands made from these components are engineered into dimeric, trimeric or tetrameric conjugates to increase functional affinity. See Tomlinson and Holliger, 2000; Carter, 2001; Hudson and Souriau, 2001; and Todorovska et al., 2001. Such conjugate structures may be created by chemical and/or genetic cross-links.

Bispecific ligands of the invention preferably are monospecific at each end, i.e., specific for a single component on minicells at one end and specific for a single component on target cells at the other end. The ligands may be multivalent at one or both ends, for example, in the form of so-called diabodies, triabodies and tetrabodies. See Hudson and Souriau, 2003. A diabody is a bivalent dimer formed by a non-covalent association of two scFvs, which yields two Fv binding sites. Likewise, a triabody results from the formation of a trivalent trimer of three scFvs, yielding three binding sites, and a tetrabody results from the formation of a tetravalent tetramer of four scFvs, yielding four binding sites.

Several humanized, human, and mouse monoclonal antibodies and fragments thereof that have specificity for receptors on mammalian cells have been approved for human therapeutic use, and the list is growing rapidly. See Hudson and Souriau, 2003. An example of such an antibody that can be used to form one arm of a bispecific ligand has specificity for HER2: Herceptin™; Trastuzumab.

Antibody variable regions also can be fused to a broad range of protein domains. Fusion to human immunoglobulin domains such as IgG1 CH3 both adds mass and promotes dimerization. See Hu et al., 1996. Fusion to human Ig hinge-Fc regions can add effector functions. Also, fusion to heterologous protein domains from multimeric proteins promotes multimerization. For example, fusion of a short scFv to short amphipathic helices has been used to produce miniantibodies. See Pack and Pluckthun, 1992. Domains from proteins that form heterodimers, such as fos/jun, can be used to produce bispecific molecules (Kostelny et al., 1992) and, alternately, homodimerization domains can be engineered to form heterodimers by engineering strategies such as "knobs into holes" (Ridgway et al., 1996). Finally, fusion protein partners can be selected that provide both multimerization as well as an additional function, e.g. streptavidin. See Dubel et al., 1995.

V. Delivery to Phagocytosis- or Endocytosis-Competent Cells

The invention further provides for delivery by means of bringing bacterially derived minicells into contact with mammalian cells that are phagocytosis- or endocytosis-competent. Such mammalian cells, which are capable of engulfing parent bacterial cells in the manner of intracellular bacterial pathogens, likewise engulf the minicells, which release their payload into the cytoplasm of the mammalian cells. This delivery approach can be effected without the use of targeting ligands.

A variety of mechanisms may be involved in the engulfing of minicells by a given type of cell, and the present invention is not dependent on any particular mechanism in this regard. For example, phagocytosis is a well-documented process in which macrophages and other phagocyte cells, such as neutrophils, ingest particles by extending pseudopodia over the particle surface until the particle is totally enveloped. Although described as "non-specific" phagocytosis, the involvement of specific receptors in the process has been demonstrated. See Wright & Jong (1986); Speert et al. (1988).

Thus, one form of phagocytosis involves interaction between surface ligands and ligand-receptors located at the membranes of the pseudopodia (Shaw and Griffin, 1981). This attachment step, mediated by the specific receptors, is thought to be dependent on bacterial surface adhesins. With respect to less virulent bacteria, such as non-enterotoxigenic *E. coli*, phagocytosis also may occur in the absence of surface ligands for phagocyte receptors. See Pikaar et al. (1995), for instance. Thus, the present invention encompasses but is not limited to the use of minicells that either possess or lack surface adhesins, in keeping with the nature of their parent bacterial cells, and are engulfed by phagocytes (i.e., "phagocytosis-competent" host cells), of which neutrophils and macrophages are the primary types in mammals.

Another engulfing process is endocytosis, by which intracellular pathogens exemplified by species of *Salmonella, Escherichia, Shigella, Helicobacter, Pseudomonas* and Lactobacilli gain entry to mammalian epithelial cells and replicate there. Two basic mechanisms in this regard are Clathrin-dependent receptor-mediated endocytosis, also known as "coated pit endocytosis" (Riezman, 1993), and Clathrin-independent endocytosis (Sandvig & Deurs, 1994). Either or both may be involved when an engulfing-competent cell that acts by endocytosis (i.e., an "endocytosis-competent" host cell) engulfs minicells in accordance with the invention. Representative endocytosis-competent cells are breast epithelial cells, enterocytes in the gastrointestinal tract, stomach epithelial cells, lung epithelial cells, and urinary tract and bladder epithelial cells.

When effecting delivery to an engulfing-competent mammalian cell without the use of a targeting ligand, the nature of the application contemplated will influence the choice of bacterial source for the minicells employed. For example, *Salmonella, Escherichia* and *Shigella* species carry adhesins that are recognized by endocytosis-mediating receptors on enterocytes in the gastrointestinal tract, and may be suitable to deliver a drug that is effective for colon cancer cells. Similarly, minicells derived from *Helicobacter pylori*, carrying adhesins specific for stomach epithelial cells, could be suited for delivery aimed at stomach cancer cells. Inhalation or insufflation may be ideal for administering intact minicells derived from a *Pseudomonas* species that carry adhesins recognized by receptors on lung epithelial cells. Minicells derived from Lactobacilli bacteria, which carry adhesins specific for urinary tract and bladder epithelial cells, could be well-suited for intraurethral delivery of a drug to a urinary tract or a bladder cancer.

VI. Formulations

The invention includes within its scope compositions, or formulations, comprising (a) an intact minicell and (b) a pharmaceutically acceptable carrier therefor, where the minicell contains a functional nucleic acid molecule or a plasmid comprising a segment that encodes a functional nucleic acid molecule. The functional nucleic acid may be any of those siRNAs, shRNAs, ribozymes or antisense molecules described herein. The functional nucleic acid also may be encoded by another nucleic acid, such as a plasmid, as described herein. The nucleic acid encoding the functional nucleic acid may have any of the regulatory elements or reporter elements, as described herein.

The formulation optionally comprise a drug, as described herein. Preferably, the minicell of the formulation contains the drug. Alternatively, the minicell may contain a nucleic acid molecule, such as a plasmid, that encodes the drug.

The minicell-containing formulations preferably contain fewer than about 1 contaminating parent bacterial cell per $10^7$ minicells, more preferably contain fewer than about 1 contaminating parent bacterial cell per $10^8$ minicells, even more preferably contain fewer than about 1 contaminating parent bacterial cell per $10^9$ minicells, still more preferably contain fewer than about 1 contaminating parent bacterial cell per $10^{10}$ minicells and most preferably contain fewer than about 1 contaminating parent bacterial cell per $10^{11}$ minicells.

The formulations also optionally contain a bispecific ligand for targeting the minicell to a target cell. The minicell and ligand may be any of those described herein. Thus, the minicell contains a nucleic acid encoding a functional nucleic acid and the bispecific ligand preferably is capable of binding to a surface component of the minicell and to a surface component of a target mammalian cell.

A formulation consisting essentially of minicells and, optionally drugs and bispecific ligands, of the present invention (that is, a formulation that includes such minicells, drugs and ligands with other constituents that do not interfere unduly with the nucleic acid or drug-delivering quality of the composition) can be formulated in conventional manner, using one or more pharmaceutically acceptable carriers or excipients.

Formulations may be presented in unit dosage form, e.g., in ampules or vials, or in multi-dose containers, with or without an added preservative. The formulation can be a solution, a suspension, or an emulsion in oily or aqueous vehicles, and may contain formulatory agents, such as suspending, stabilizing and/or dispersing agents. A suitable solution is isotonic with the blood of the recipient and is illustrated by saline, Ringer's solution, and dextrose solution. Alternatively, formulations may be in lyophilized powder form, for reconstitution with a suitable vehicle, e.g., sterile, pyrogen-free water or physiological saline. The formulations also may be in the form of a depot preparation. Such long-acting formulations may be administered by implantation (for example, subcutaneously or intramuscularly) or by intramuscular injection.

A. Administration Routes

Formulations of the invention can be administered via various routes and to various sites in a mammalian body, to achieve the therapeutic effect(s) desired, either locally or systemically. Delivery may be accomplished, for example, by oral administration, by application of the formulation to a body cavity, by inhalation or insufflation, or by parenteral, intramuscular, intravenous, intraportal, intrahepatic, peritoneal, subcutaneous, intratumoral, or intradermal administration. The mode and site of administration is dependent on the location of the target cells. For example, cystic-fibrotic cells may be efficiently targeted by inhaled delivery of the targeted minicells. Similarly, tumor metastasis may be more efficiently treated via intravenous delivery of targeted minicells. Primary ovarian cancer may be treated via intraperitoneal delivery of targeted minicells.

B. Purity

Minicells of the invention are substantially free from contaminating parent bacterial cells. Thus, minicell-containing formulations of the invention preferably contain fewer than about 1 contaminating parent bacterial cell per $10^7$ minicells, more preferably contain fewer than about 1 contaminating parent bacterial cell per $10^8$ minicells, even more preferably contain fewer than about 1 contaminating parent bacterial cell per $10^9$ minicells, still more preferably contain fewer than about 1 contaminating parent bacterial cell per $10^{10}$ minicells and most preferably contain fewer than about 1 contaminating parent bacterial cell per $10^{11}$ minicells.

Methods of purifying minicells are known in the art and described in PCT/IB02/04632. One such method combines cross-flow filtration (feed flow is parallel to a membrane surface; Forbes, 1987) and dead-end filtration (feed flow is perpendicular to the membrane surface). Optionally, the filtration combination can be preceded by a differential centrifugation, at low centrifugal force, to remove some portion of the bacterial cells and thereby enrich the supernatant for minicells.

Another purification method employs density gradient centrifugation in a biologically compatible medium. After centrifugation, a minicell band is collected from the gradient, and, optionally, the minicells are subjected to further rounds of density gradient centrifugation to maximize purity. The method may further include a preliminary step of performing differential centrifugation on the minicell-containing sample. When performed at low centrifugal force, differential centrifugation will remove some portion of parent bacterial cells, thereby enriching the supernatant for minicells.

Particularly effective purification methods exploit bacterial filamentation to increase minicell purity. Thus a minicell purification method can include the steps of (a) subjecting a sample containing minicells to a condition that induces parent bacterial cells to adopt a filamentous form, followed by (b) filtering the sample to obtain a purified minicell preparation.

Known minicell purification methods also can be combined. One highly effective combination of methods is as follows:

Step A: Differential centrifugation of a minicell producing bacterial cell culture. This step, which may be performed at 2000 g for about 20 minutes, removes most parent bacterial cells, while leaving minicells in the supernatant.

Step B: Density gradient centrifugation using an isotonic and non-toxic density gradient medium. This step separates minicells from many contaminants, including parent bacterial cells, with minimal loss of minicells. Preferably, this step is repeated within a purification method.

Step C: Cross-flow filtration through a 0.45 µm filter to further reduce parent bacterial cell contamination.

Step D: Stress-induced filamentation of residual parent bacterial cells. This may be accomplished by subjecting the minicell suspension to any of several stress-inducing environmental conditions.

Step E: Antibiotic treatment to kill parent bacterial cells.

Step F: Cross-flow filtration to remove small contaminants, such as membrane blebs, membrane fragments, bacterial debris, nucleic acids, media components and so forth, and to concentrate the minicells. A 0.2 µm filter may be employed to separate minicells from small contaminants, and a 0.1 µm filter may be employed to concentrate minicells.

Step G: Dead-end filtration to eliminate filamentous dead bacterial cells. A 0.45 um filter may be employed for this step.

Step H: Removal of endotoxin from the minicell preparation. Anti-Lipid A coated magnetic beads may be employed for this step.

C. Administration Schedules

In general, the formulations disclosed herein may be used at appropriate dosages defined by routine testing, to obtain optimal physiological effect, while minimizing any potential toxicity. The dosage regimen may be selected in accordance with a variety of factors including age, weight, sex, medical condition of the patient; the severity of the condition to be treated, the route of administration, and the renal and hepatic function of the patient.

Optimal precision in achieving concentrations of minicell and drug within the range that yields maximum efficacy with minimal side effects may require a regimen based on the kinetics of the minicell and drug availability to target sites and target cells. Distribution, equilibrium, and elimination of a minicell or drug may be considered when determining the optimal concentration for a treatment regimen. The dosages of the minicells and drugs may be adjusted when used in combination, to achieve desired effects.

Moreover, the dosage administration of the formulations may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See, e.g., WO 00/67776.

Specifically, the formulations may be administered at least once a week over the course of several weeks. In one embodiment, the formulations are administered at least once a week over several weeks to several months.

More specifically, the formulations may be administered at least once a day for about 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days. Alternatively, the formulations may be administered about once every day, about once every 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days or more.

The formulations may alternatively be administered about once every week, about once every 2, 3, 4, 5, 6, 7, 8, 9, 10, 11, 12, 13, 14, 15, 16, 17, 18, 19 or 20 weeks or more. Alternatively, the formulations may be administered at least once a week for about 2, 3, 4, 5, 6, 7, 8, 9, 10, 11, 12, 13, 14, 15, 16, 17, 18, 19 or 20 weeks or more.

Alternatively, the formulations may be administered about once every month, about once every 2, 3, 4, 5, 6, 7, 8, 9, 10, 11 or 12 months or more.

The formulations may be administered in a single daily dose, or the total daily dosage may be administered in divided doses of two, three, or four times daily.

In method in which minicells are administered before a drug, administration of the drug may occur anytime from several minutes to several hours after administration of the minicells. The drug may alternatively be administered anytime from several hours to several days, possibly several weeks up to several months after the minicells.

More specifically, the minicells may be administered at least about 1, 2, 3, 4, 5, 6, 7, 8, 9, 10, 11, 12, 13, 14, 15, 16, 17, 18, 19, 20, 21, 22, 23 or 24 hours before the drug. Moreover, the minicells may be administered at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days before the administration of the drug. In yet another embodiment, the minicells may be administered at least about 1, 2, 3, 4, 5, 6, 7, 8, 9, 10, 11, 12, 13, 14, 15, 16, 17, 18, 19 or 20 weeks or more before the drug. In a further embodiment, the minicells may be administered at least about 1, 2, 3, 4, 5, 6, 7, 8, 9, 10, 11 or 12 months before the drug.

In another embodiment, the minicell is administered after the drug. The administration of the minicell may occur anytime from several minutes to several hours after the administration of the drug. The minicell may alternatively be administered anytime from several hours to several days, possibly several weeks up to several months after the drug.

The following examples are illustrative only, rather than limiting, and provide a more complete understanding of the invention. The examples demonstrate that drug resistant tumor cells can be effectively treated in-vivo by (1) administration of targeted recombinant minicells carrying RNAi sequences designed to reduce or eliminate expression of drug resistance encoding gene(s), and (2) administration of targeted, drug-packaged minicells carrying the drug to which the cancer cells are made sensitive.

Example 1. Anti-MDR1 and Anti-Bcl-2 shRNA Expression Plasmids and Purification of Recombinant Minicells Recombinant minicells carrying plasmids encoding shRNA sequences (Mdr1 or bcl-2) were generated as follows. The Mdr1 shRNA sequence used in this study was described by Wu et al., 2003 (5'-TCGA AAGAAAC-CAACTGTCAGTGTA gagtactg TACACTGACAGTTG-GTTTCTT TTTTT-3') (SEQ ID NO: 1) and the bcl-2 shRNA sequence used was described by Wacheck et al., 2003 (5'-TCGATGTGGATGACTGAGTACCTGA gagtactg TCAGGTACTCAGTCATCCACATTTTT-3') (SEQ ID NO: 2). The respective shRNA sequences were synthesized and individually subcloned into plasmid IMG-800 (Imgenex Corp., San Diego, Calif., USA) such that the sequences could be expressed from the plasmid U6 promoter. The plasmid carries the pUC origin of replication which enables high plasmid copy numbers in bacterial cells. The recombinant plasmids were sequenced to ensure that the shRNA sequences were correct and in-frame for expression from the U6 promoter. The recombinant plasmids were transformed into the *S. typhimurium* minCDE-mutant strain and minicells carrying the plasmids were purified as described in U.S. Ser. No. 10/602,201. The recombinant minicells were designated minicells$_{shRNA\text{-}MDR1}$ and minicells$_{shRNA\text{-}bcl2}$ respectively.

Example 2. Demonstration of Receptor-Targeted Recombinant Minicell-Mediated shRNA Plasmid Delivery to Drug Resistant Cancer Cells and Reversal of Drug Resistance In-Vitro While siRNAs directed against a range of different drug-resistance encoding transcripts have been shown to reverse drug resistance in cancer cells in-vitro, the critical hurdle is targeted delivery of the siRNAs into cancer cells, particularly in-vivo. Recombinant minicells carrying anti-MDR1 shRNA plasmid (minicells$_{shRNA\text{-}MDR1}$) and control shRNA against a nonsense RNA sequence (minicells$_{shRNA\text{-}nonsense}$) were purified and bispecific antibody carrying anti-*S. typhimurium* O-antigen and anti-human EGFR specificities was prepared and attached to the recombinant minicells, as described in patent application WO 2005/056749. The targeted recombinant minicells were designated $^{EGFR}$minicells$_{shRNA\text{-}MDR\text{-}1}$ and $^{EGFR}$minicells$_{shRNA\text{-}nonsense}$. Minicells packaged with chemotherapeutic drugs 5-FU and irinotecan were also prepared and targeted as above and were designated $^{EGFR}$minicells$_{5\text{-}FU}$ and $^{EGFR}$minicells$_{Irino}$ respectively.

Human colon cancer cell line Caco-2 (ATCC), which is highly resistant to irinotecan and 5-FU, was selected for this in-vitro study to determine firstly, if EGFR-targeted recombinant minicells could successfully deliver the shRNA plasmids to the cancer cells and secondly, if the expression of anti-MDR-1 siRNA could reverse the drug resistance and make the Caco-2 cells sensitive to EGFR-targeted and drug-packaged minicells. Caco-2 cells were seeded at $3 \times 10^6$ cells/flask in Minimum Essential Medium with 10% cosmic calf serum and incubated for 3 hours at 37° C., 5% $CO_2$.

The cells were treated with (a) $^{EGFR}$minicells$_{shRNA-MDR-1}$, and (b) $^{EGFR}$minicells$_{shRNA-nonsense}$. A control flask was included that did not receive any treatment. Minicells were added at a concentration of $10^{10}$ per flask and all flasks were incubated for 72 hrs. The cells from each treatment were trypsinised and seeded at $1 \times 10^4$ cells/ml/well in 24-well plates and were incubated for 3 hrs at 37° C., 5% $CO_2$. The control untreated cells were then incubated with (6 wells/treatment) (a) free irinotecan (25 µM), (b) free 5-FU (25 µM), (c) $^{EGFR}$minicells$_{Irino}$, and (d) $^{EGFR}$minicells$_{5-FU}$.

The $^{EGFR}$minicells$_{shRNA-MDR-1}$ treated Caco-2 cells were incubated with (6 wells/treatment) (a) $^{CMV}$minicells$_{5-FU}$ (non-specifically targeted since the bispecific antibody is targeted to a surface protein on cytomegalovirus), (b) free irinotecan, (c) free 5-FU EGFR, (d) $^{EGFR}$minicells$_{Irino}$, and (e) $^{EGFR}$minicells$_{5-FU}$. The $^{EGFR}$minicells$_{shRNA-nonsense}$ treated Caco-2 cells were then treated with $_{EGFR}$minicells$_{5-FU}$.

All cells were incubated for a further 72 hrs followed by the colorimetric MTT cell proliferation assay (Cory et al., 1991) using the CellTiter 96 AQ$_{ueous}$ One Solution Cell Proliferation Assay (Promega Corp., Madison, Wis., USA), according to the manufacturer's instructions. The colorimetric measurements were read at 490 nm.

The results showed (FIG. 1) that the Caco-2 cells were highly resistant to first-line chemotherapy drugs for colon cancer, i.e., irinotecan and 5-FU. Additionally, the cells remained resistant following treatments with $_{EGFR}$minicells$_{Irino}$, $^{EGFR}$minicells$_{5-FU}$ and $^{EGFR}$minicells$_{shRNA-MDR-1}$. Cells that received the dual treatment, i.e., $^{EGFR}$minicells$_{shRNA-MDR-1}$ followed by $^{EGFR}$minicells$_{Irino}$ or $^{EGFR}$minicells$_{5-FU}$ showed that this treatment was highly successful in reversing the drug resistance and after a single combination treatment >50% cell death was observed. In contrast, a dual treatment of $^{EGFR}$minicells$_{shRNA-nonsense}$ followed by $^{EGFR}$minicells$_{5-FU}$ had no effect on drug resistance, suggesting that the anti-MDR-1 shRNA expression in the Caco-2 cells was specifically responsible for the reversal of drug resistance. The combination treatment of $^{EGFR}$minicells$_{shRNA-MDR-1}$ followed by free irinotecan or 5-FU was also effective in reversal of drug resistance but to a lesser extent giving ~30% reduction in cell survival. This data also suggests that chemotherapeutic drug delivery via receptor-targeted and drug-packaged minicells may deliver a more potent concentration of drug intracellularly compared to free drug provided in the extracellular environment.

This result demonstrated that (a) shRNAs can be effectively delivered to non-phagocytic mammalian cells via receptor-targeted recombinant minicells, (b) functional nucleic acid (shRNA) encoding plasmids escape from intracellular organelles where the minicells are broken down, (c) the plasmid is transported to the mammalian cell nucleus where the shRNA is expressed, (d) the shRNA is effective in degrading the mRNA encoding multi-drug resistance protein, MDR-1, (e) the same mammalian cells are receptive to the next wave of receptor-targeted minicells which now carry a drug instead of a plasmid, (f) the dual treatment protocol, i.e., receptor-targeted minicell-mediated shRNA delivery followed by receptor-targeted minicell-mediated chemotherapeutic drug delivery is highly effective in reversing drug resistance in non-phagocytic mammalian cells.

Example 3. In-Vivo Demonstration of Tumor Regression Achieved Using the Method of Invention i.e. Dual Treatment of Receptor-Targeted Minicell-Mediated shRNA Delivery Followed by Receptor-Targeted Minicell-Mediated Drug Delivery This example demonstrates that receptor-targeted minicells can be used to reverse drug resistance in cancer cells in-vivo.

*S. typhimurium* minCDE-derived minicells were purified and packaged with chemotherapeutic drug irinotecan. $7 \times 10^9$ minicells in BSG solution were centrifuged, the supernatant was discarded and the minicells were resuspended in 940 µl BSG and 60 µl of irinotecan solution (1 mg/ml; dissolved in sterile distilled water). The suspension was incubated overnight at 37° C. with rotation to allow the irinotecan to diffuse into the minicell cytoplasm. Excess irinotecan non-specifically attached to the outer surface of the minicells was then washed away by stirred cell ultrafiltration as follows. Amicon stirred ultrafiltration cell Model 8010 (Millipore, Billerica, Mass., USA) was assembled according to the manufacturer's instructions with an ultrafiltration membrane disc (polyethersulfone; molecular weight cut-off of 300 kDa; Millipore). The cell was washed three times with sterile distilled water followed by a further three washes with BSG. The cell was then filled with 9 ml of fresh BSG and the 1 ml solution of irinotecan-packaged minicells was added. The cell was kept under a pressure of 10 psi, stirred until the volume was reduced to 5 ml and topped-off with 5 ml BSG. Ultrafiltration was continued until the volume again dropped to 5 ml. This topping-off/ultrafiltration procedure was performed 6 times to enable a thorough washing of the exterior surfaces of the irinotecan-packaged minicells. During the last ultrafiltration, the volume was reduced to 1 ml and the sample was transferred to a sterile Eppendorf centrifuge tube, followed by centrifugation at 13,200 rpm for 10 minutes to pellet the irinotecan-packaged minicells.

A bispecific antibody was constructed as described above and in U.S. published Patent Application No. 2004-0265994. Briefly, anti-*S. typhimurium* lipopolysaccharide (Biodesign, Saco, Me., USA) and anti-human Epidermal Growth Factor Receptor (EGFR) mouse monoclonal antibodies (Oncogene Research Products, Cambridge, Mass., USA) were linked to purified recombinant protein A/G via the Fc fragments of each monoclonal antibody. An anti-EGFR monoclonal antibody was selected because the xenografted cells were human colon cancer cells (Caco-2) that are known to overexpress the EGFR on the cell surface (Nyati et al., 2004).

Purified recombinant protein A/G (Pierce Biotechnology, Rockford, Ill., USA) was diluted to a final concentration of 100 µg/ml in Immunopure binding buffer (Pierce Biotechnology) and 0.5 ml of the solution was incubated overnight at 4° C. with a premixed solution containing 20 µg/ml each of anti-*S. typhimurium* LPS and anti-human EGFR monoclonal antibodies. The excess antibodies unbound to protein A/G were then removed as follows. Dynabeads® Protein G solution (Dynabeads® [2.8 µm] coated with recombinant Protein G covalently coupled to the surface of the magnetic particles; Dynal Biotech, Oslo, Norway) was mixed gently and 100 µl of the solution was transferred into an Eppendorf centrifuge tube. The tube was placed in a Dynal MPC-S (Magnetic Particle Concentrator, type S) to immobilize the beads and the supernatant was discarded. The beads were resuspended in 0.5 ml of washing solution containing 0.1M Na-phosphate buffer (pH 5.0). The bead immobilization and washing steps were repeated three times. The solution containing protein A/G-bispecific antibody mixture was added to the beads and incubated with gentle mixing at room temperature for 40 min. The tube was placed on the MPC-S stand to immobilize the beads and the protein A/G-bispecific antibody was removed with a pipette. This step eliminated the unbound excess monoclonal antibodies and provided a solution that carried the bispecific antibody linked to protein A/G via their Fc fragments. Recombinant minicells were incubated with the protein A/G-bispecific antibody for 1 hr at room temperature, to coat the minicells with the antibody via its anti-LPS Fab region.

The mice used in this example were purchased from Animal Resources Centre, Perth, Wash., Australia, and all animal experiments were performed in compliance with the guide of care and use of laboratory animals and with Animal Ethics Committee approval. The experiments were performed in the NSW Agriculture accredited small animal facility at EnGeneIC Pty Ltd (Sydney, NSW, Australia). Human colon cancer cells (Caco-2, ATCC) were grown in tissue culture in RPMI 1640 medium supplemented with 5% Bovine Calf Serum (GIBCO-BRL Life Technologies, Invitrogen Corporation, Carlsbad, Calif., USA) and glutamine (Invitrogen) in a humidified atmosphere of 95% air and 5% $CO_2$ at 37° C. $1 \times 10^6$ cells in 50 µl serum-free media together with 50 µl growth factor reduced matrigel (BD Biosciences, Franklin Lakes, N.J., USA) were injected subcutaneously between the shoulder blades of each mouse using a 23-gauge needle. The tumors were measured twice a week using an electronic digital caliper (Mitutoyo, Japan, precision to 0.001) and mean tumor volume was calculated using the formula, length (mm)×width$^2$ (mm)×0.5=volume (mm)$^3$. The various treatments commenced once the tumors reached volumes between 50 mm$^3$ and 80 mm$^3$, and mice were randomized to eight different groups of 11 per group.

The various groups received the following treatments: Group 1 (control) received no treatment. Group 2 (control), free irinotecan ($1.2 \times 10^4$ ng/gm of mouse body weight ~$2.4 \times 10^5$ ng per mouse) intravenously. This control was included to confirm the in-vitro results that the tumor cells were resistant to the drug. Group 3 (control), EGFR-targeted, irinotecan-packaged minicells (designated $^{EGFR}$minicells$_{Irino}$). Group 4 (control), $^{EGFR}$minicells$_{shRNA-MDR-1}$. Group 5 (control), $^{EGFR}$minicells$_{shRNA-bcl-2}$. Group 6 (control), $^{EGFR}$minicells$_{shRNA-MDR-1}$ followed by free irinotecan. Group 7 (experimental), $^{EGFR}$minicells$_{shRNA-MDR-1}$ followed by $^{EGFR}$minicells$_{Irino}$. Group 8 (expt.), $^{EGFR}$minicells$_{shRNA-bcl-2}$ followed by $^{EGFR}$minicells$_{Irino}$. Irinotecan quantitation studies by HPLC showed that $5 \times 10^8$ minicells packaged ~80 ng of the drug. All minicell treatments received $5 \times 10^8$ minicells and shRNA treatments were administered on days 9 and 23. All drug treatments were administered on days 15, 18, 29 and 32. This allowed a six day interval between shRNA and drug treatments to ensure that sufficient time was allowed for intracellular and nuclear delivery of shRNA, gene expression and suppression of expression of the drug resistance mediating protein, i.e., either MDR-1 or bcl-2.

Figure 2:
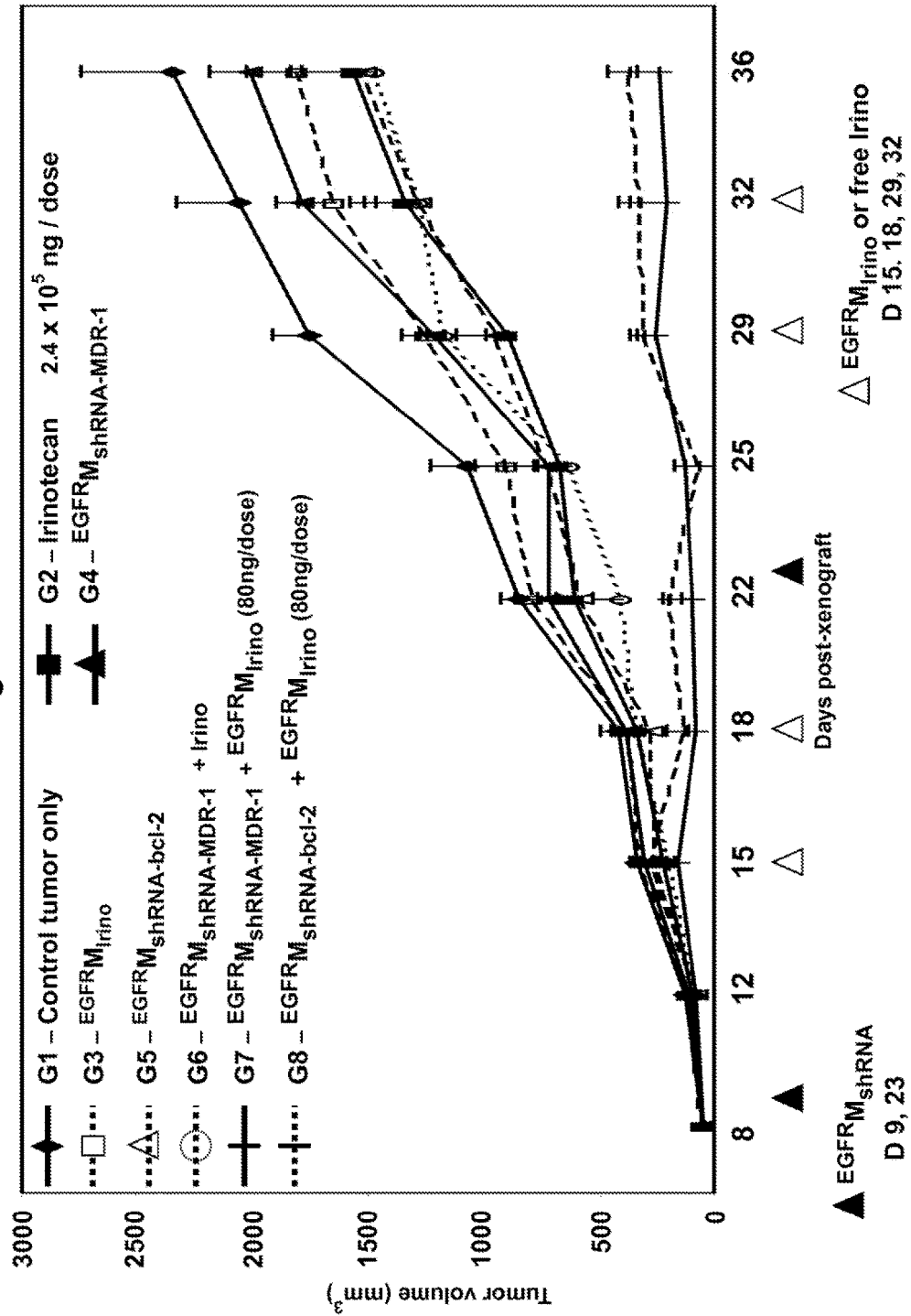
FIG. 2 shows regression of human colon cancer (Caco-2) xenografts in nude mice (11 mice per group) following dual treatment with (1) targeted recombinant minicells carrying shRNA encoding plasmids (anti-bcl2 or anti-Mdr1) and (2) targeted minicells packaged with the chemotherapeutic drug Irinotecan. The bispecific antibody used to target the colon cancer cells carried specificity against S. typhimurium O-antigen on one arm and human epidermal growth factor receptor (EGFR) on the other arm. The targeted recombinant minicells were injected intravenously on days 9 and 23, and the targeted Irinotecan packaged minicells were given intravenously on days 15, 18, 29 and 32. Other control treatments administered intravenously include: Group 1—tumor only, Group 2—free irinotecan, Group 3—$^{EGFR}$minicells$_{Irino}$, Group 4—$^{EGFR}$minicells$_{shRNA\text{-}MDR\text{-}1}$, Group 5—$^{EGFR}$minicells$_{shRNA\text{-}bcl\text{-}2}$ and Group 6—$^{EGFR}$minicells$_{shRNA\text{-}MDR\text{-}1}$ followed by free Irino. Tumor volume is shown on the y-axis. SEM is shown for each measurement.

The results revealed (FIG. 2) a striking contrast between the mean tumor volumes in control groups (G1 to 6) and experimental groups (G7 and 8). The tumor volumes in the experimental groups were rapidly stabilized and showed significant stabilization in most of the 11 animals in each group. In contrast, the mean tumor volumes in all the different control groups continued to rise and by day 36 post-xenograft establishment the experiment was terminated because the control animals were too sick. The experimental animals, on the other hand, were healthy and did not show any toxic side effects of the treatment. Statistical analysis of the data using one-way ANOVA showed that experimental groups (7 and 8) were highly significant compared to the control groups 1 to 6 (p=0.0004). This result is a first demonstration of targeted in-vivo delivery of shRNA to address the serious problem of drug resistance in cancer. The result also demonstrated that the invention has general application, because two mechanistically different methods of drug resistance, i.e., over-expressed membrane-associated protein pump (MDR-1) and cytoplasmic anti-apoptosis protein (bcl-2), can be down-regulated in drug-resistant cancer cells in-vivo. Treating the same cells with another wave of receptor-targeted, chemotherapeutic drug-packaged minicells could effectively treat such tumors.

Example 4. Second In-Vivo Demonstration of Tumor Regression Efficacy Achieved Using the Method of Invention i.e. Dual Treatment of Minicell-Mediated shRNA Delivery Followed by Minicell-Mediated Drug Delivery Colorectal cancer cells are also known to be highly resistant to another first-line chemotherapeutic drug, 5-fluorouracil (5-FU), and this example shows that the methods of the invention enable not only the reversal of drug resistance in-vivo but also permit tumor stabilization/regression.

As described above, minicells were obtained from an *S. typhimurium* minCDE-mutant strain and were purified using the gradient centrifugation/filamentation/filtration/endotoxin removal procedure. Similarly recombinant minicells carrying shRNA plasmids, shRNA-MDR-1, shRNA-bcl-2 and shRNA-nonsense were obtained and purified from the respective *S. typhimurium* minCDE-recombinant strains. The purified empty minicells were packaged with chemotherapeutic drug 5-FU as described for irinotecan in Example 3. HPLC analysis was used to determine the concentration of 5-FU packaged in the mincells.

A bispecific antibody comprising anti-human EGFR and anti-*S. typhimurium* O-antigen dual specificities was constructed as described in Example 3. Recombinant minicells ($10^{10}$) were incubated with the bispecific antibody for 1 hour at room temperature, to coat the minicells with the antibody via its anti-O-antigen Fab region.

Caco-2 cancer cell xenografts were established in Balb/c nude mice and once the tumors reached a volume between 50 mm$^3$ and 80 mm$^3$, mice were randomized into 10 groups (n=11 mice per group). The 10 intravenous treatments included: (a) G1—tumor only control. G2 (control), free 5-FU ($5 \times 10^4$ ng/gm of mouse body weight ~$1 \times 10^6$ ng per mouse). This control was included to confirm the in-vitro results that the tumor cells were resistant to the drug. G3 (control), EGFR-targeted, 5-FU-packaged minicells (designated $^{EGFR}$minicells$_{5-FU}$). G4 (control), $^{EGFR}$minicells$_{shRNA-MDR-1}$. G5 (control), $^{EGFR}$minicells$_{shRNA-bcl-2}$. G6 (control), $^{EGFR}$minicells$_{shRNA-MDR-1}$ followed by $^{CMV}$minicells$_{5-FU}$. The CMV antibody is targeted to a surface protein on cytomegalovirus and this serves as a non-specifically targeted control. G7 (control), $^{EGFR}$minicells$_{shRNA-nonsense}$ followed by $^{EGFR}$minicells$_{5-FU}$. G8 (control), $^{EGFR}$minicells$_{shRNA-MDR-1}$ followed by free 5-FU, G9 (expt), $^{EGFR}$minicells$_{shRNA-MDR-1}$ followed by $^{EGFR}$minicells$_{5-FU}$. G10 (expt), $^{EGFR}$minicells$_{shRNA-bcl-2}$ followed by $^{EGFR}$minicells$_{5-FU}$. The shRNA treatments were administered on days 9 and 23 and drug treatments were administered on days 15, 18, 29 and 32. This allowed a six day interval between shRNA and drug treatments to ensure that sufficient time was allowed for intracellular and nuclear delivery of shRNA, gene expression and suppression of expression of the drug resistance mediating protein, i.e., either MDR-1 or bcl-2.

Figure 3:
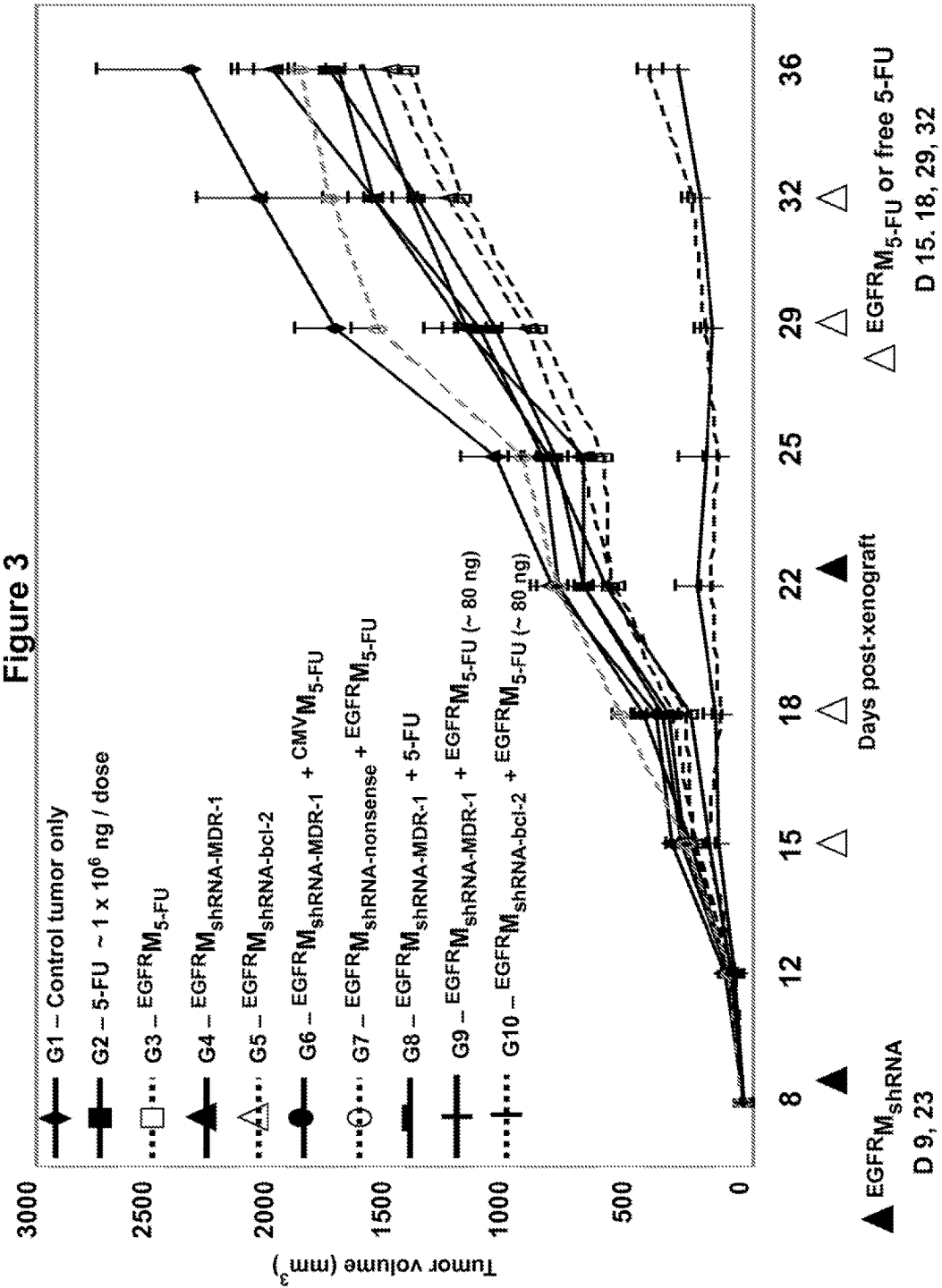
FIG. 3 shows regression of human colon cancer (Caco-2) xenografts in nude mice (11 mice per group) following dual treatment with (1) targeted recombinant minicells carrying shRNA encoding plasmids (anti-bcl2 or anti-Mdr1) and (2) targeted minicells packaged with the chemotherapeutic drug 5-FU. The bispecific antibody used to target the colon cancer cells carried specificity against S. typhimurium O-antigen on one arm and human epidermal growth factor receptor (EGFR) on the other arm. The targeted recombinant minicells were injected intravenously on days 9 and 23, and the targeted 5-FU packaged minicells were given intravenously on days 15, 18, 29 and 32. Other control treatments administered intravenously include: G1—tumor only, G2 (control), free 5-FU ($5 \times 10^4$ ng/gm of mouse body weight ~$1 \times 10^6$ ng per mouse), G3 (control), $^{EGFR}$minicells$_{5-FU}$, G4 (control), $^{EGFR}$minicells$_{shRNA-MDR-1}$, G5 (control), $^{EGFR}$minicells$_{shRNA-bcl-2}$, G6 (control), $^{EGFR}$minicells$_{shRNA-MDR-1}$ followed by $^{CMV}$minicells$_{5-FU}$, G7 (control), $^{EGFR}$minicells$_{shRNA-nonsense}$ followed by $^{EGFR}$minicells$_{5-FU}$, G8 (control), $^{EGFR}$minicells$_{shRNA-MDR-1}$ followed by free 5-FU, G9 (expt), $^{EGFR}$minicells$_{shRNA-MDR-1}$ followed by $^{EGFR}$minicells$_{5-FU}$, and G10 (expt), $^{EGFR}$minicells$_{shRNA-bcl-2}$ followed by $^{EGFR}$minicells$_{5-FU}$. Tumor volume is shown on the y-axis. SEM is shown for each measurement.

The results revealed (FIG. 3) a striking contrast between the mean tumor volumes in control groups (G1 to 8) and experimental groups (G9 and 10). The tumor volumes in the experimental groups showed significant stabilization in most of the 11 animals in each group. In contrast, the mean tumor volumes in all the different control groups continued to rise and by day 36 post-xenograft establishment the experiment was terminated because the control animals were too sick. The experimental animals, on the other hand, were healthy and did not show any toxic side effects of the treatment. Statistical analysis of the data using one-way ANOVA showed that experimental groups (9 and 10) were highly significant compared to the control groups 1 to 8 ($p=0.0008$).

Example 5. In-Vivo Demonstration of Tumor Regression Achieved in Doxorubicin Resistant Human Breast Cancer Cells Using the Method of Invention The inventors have shown that human breast adenocarcinoma cell line, MDA-MB-468 is highly sensitive to doxorubicin and that mouse xenografts treated intravenously with $^{EGFR}$minicells$_{Dox}$ stabilize/regress.

In this example, MDA-MB-468 cells were cultivated in tissue culture and treated with increasing concentrations of Dox to develop a Dox-resistant clone. It is well established that such drug treatment in-vitro and in-vivo up-regulates the expression of multi-drug resistance proteins such as MDR-1 and bcl-2. Several Dox-resistant clones were obtained and one was used to establish a xenograft in Balb/c nude mice. The intravenous treatment groups (n=11 mice per group) included G2—$^{EGFR}$minicells$_{Dox}$ and G3—$^{EGFR}$minicells$_{shRNA-MDR-1}$ followed by $^{EGFR}$minicells$_{Dox}$. G1 mice were tumor only control. The shRNA treatment was administered on day 21 and the drug treatments were given on days 27, 34 and 41.

Figure 4:
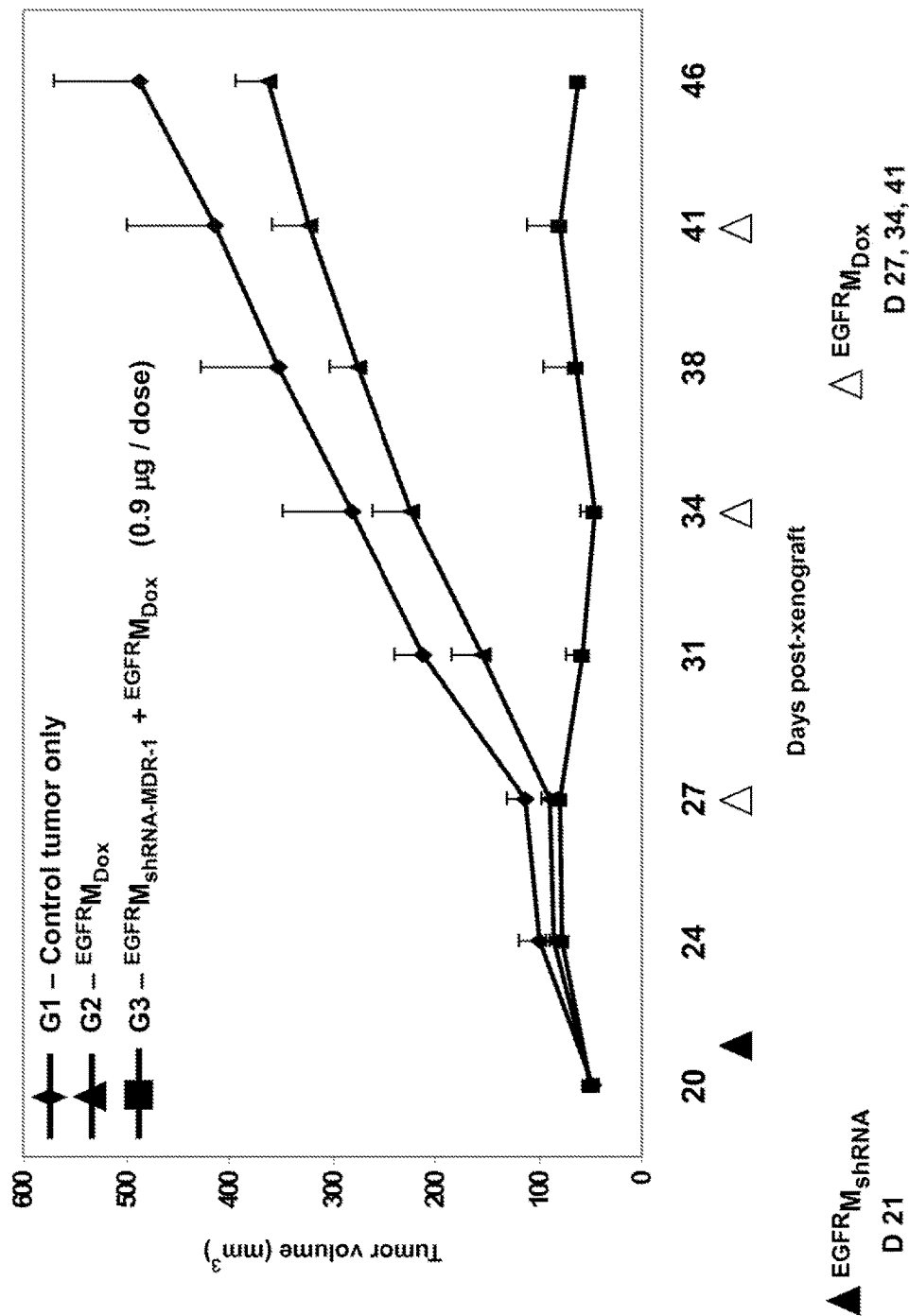
FIG. 4 shows regression of human breast cancer (MDA-MB-468) xenografts in nude mice (11 mice per group) following dual treatment with (1) targeted recombinant minicells carrying shRNA encoding plasmid (anti-MDR-1) and (2) targeted minicells packaged with chemotherapeutic drug doxorubicin. The bispecific antibody used to target the breast cancer cells carried specificity against S. typhimurium O-antigen on one arm and human EGFR on the other arm. The targeted recombinant minicells were injected intravenously on day 21 and the targeted Dox-packaged minicells were given intravenously on days 27, 34 and 41. Treatments administered intravenously include: G1—tumor only, G2 (control), $^{EGFR}$minicells$_{Dox}$, and G3 (expt), $^{EGFR}$minicells$_{shRNA-MDR-1}$ followed by $^{EGFR}$minicells$_{Dox}$. Tumor volume is shown on the y-axis. SEM is shown for each measurement.

The results showed (FIG. 4) that the $^{EGFR}$minicells$_{shRNA-MDR-1}$ followed by $^{EGFR}$minicells$_{Dox}$ treatment in G3 mice was highly effective in reversing Dox resistance in the cancer cells and that the tumors were stabilized. The control treatment with $^{EGFR}$minicells$_{Dox}$ (G2) showed that the tumor cells were highly resistant to Dox and the tumors grew rapidly.

Example 6. In-Vivo Demonstration of Effect of Dosing Schedules on Reversal of Drug Resistance and Therapeutic Effect This example demonstrates the effect of dosing schedules on the reversal of drug resistance and therapeutic effect. Allowing sufficient time for efficient delivery of shRNA to the tumor cells before the receptor-targeted, drug-packaged minicells are administered improves the results. A time-course experiment was performed, wherein $^{EGFR}$minicells$_{shRNA-MDR-1}$ were administered intravenously in nude mice carrying Caco-2 cell xenograft. In separate groups (n=11 mice per group), mice were given $^{EGFR}$minicells$_{Irino}$ either at 96 hr (G3), 120 hr (G4) or 144 hr (G5) after the $^{EGFR}$minicells$_{shRNA-MDR-1}$ treatment. G1 and G2 were tumor only and free irinotecan (~$2.4\times10^5$ ng/dose) controls. The minicells were administered at $5\times10^8$ per dose and each dose carried ~80 ng of irinotecan packaged in minicells, which is a 3,000-fold lower dose than that administered as free drug. The results showed (FIG. 5) a clear correlation between the time allowed for shRNA expression and subsequent administration of $^{EGFR}$minicells$_{Irino}$ with 144 hr (G5) being most effective in reversing drug resistance and achieving a significant therapeutic effect.

Example 7. Second In-Vivo Demonstration of Effect of Dosing Schedules on Reversal of Drug Resistance and Therapeutic Effect This example demonstrates that the dosing schedule effect observed in example 6 is broadly applicable.

The experiment described in example 6 was repeated with the same controls and experimental groups except that G2 received free 5-FU ($1\times10^6$ ng/dose) and in G3, G4 and G5, the second treatment was carried out with $^{EGFR}$minicells$_{5-FU}$. Minicells were administered at $1\times10^9$ per dose and each dose carried ~80 ng 5-FU, i.e., ~12,500-fold lower than free drug administration in G2 mice.

Figure 5:
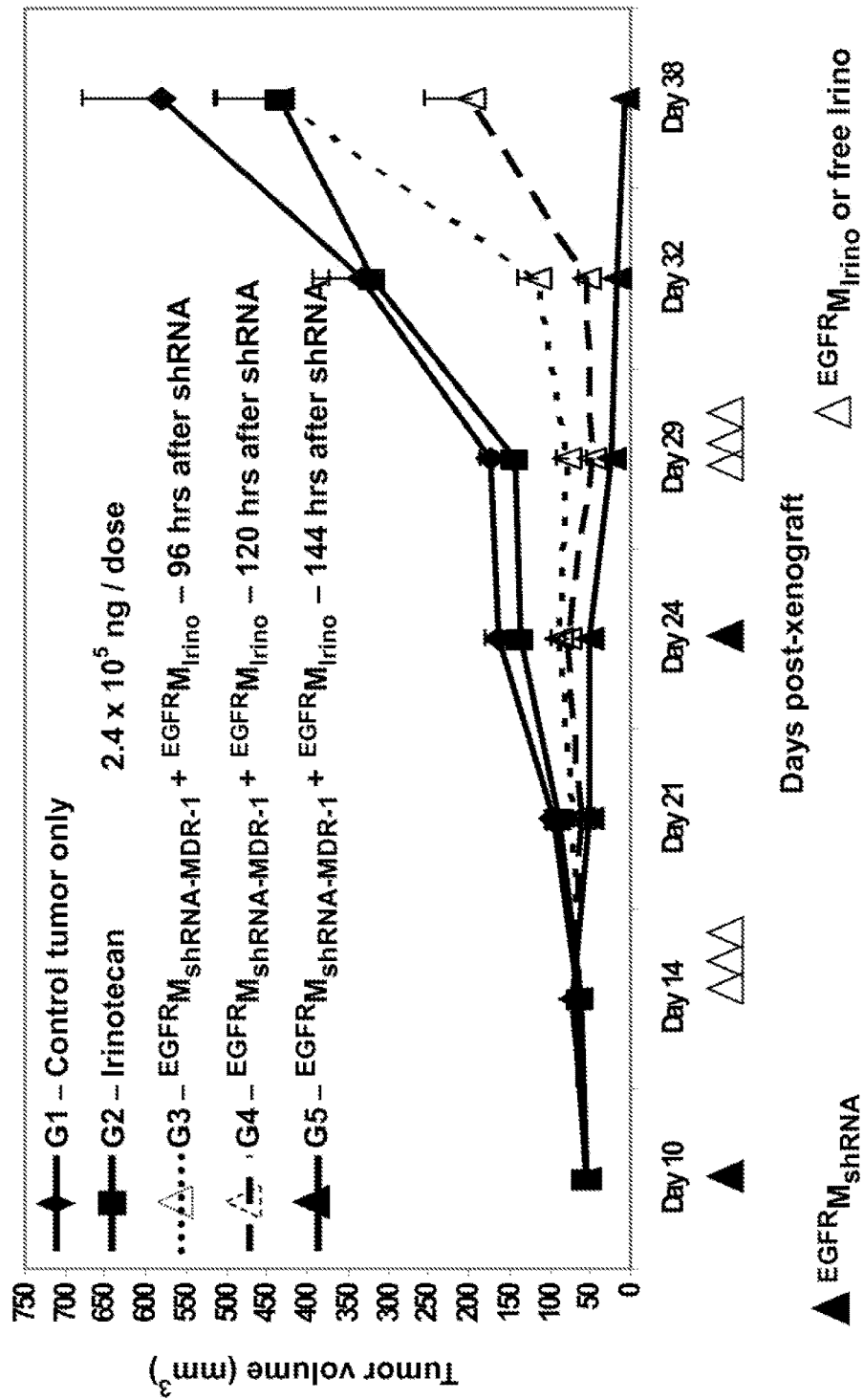
FIG. 5 shows the effect of dosing schedules on reversal of drug-resistance and therapeutic effect. Human colon cancer (Caco-2) xenografts were established in nude mice and the following intravenous treatments were administered: G1—tumor only, G2 (control), free irinotecan, G3 (expt), $^{EGFR}$minicells$_{shRNA-MDR-1}$ followed 96 hrs later by $^{EGFR}$minicells$_{Irino}$, G4 (expt), $^{EGFR}$minicells$_{shRNA-MDR-1}$ followed 120 hrs later by $^{EGFR}$minicells$_{Irino}$, and G5 (expt), $^{EGFR}$minicells$_{shRNA-MDR-1}$ followed 144 hrs later by $^{EGFR}$minicells$_{Irino}$. The bispecific antibody used to target the breast cancer cells carried specificity against S. typhimurium O-antigen on one arm and human EGFR on the other arm. Tumor volume is shown on the y-axis. SEM is shown for each measurement.
Figure 6:
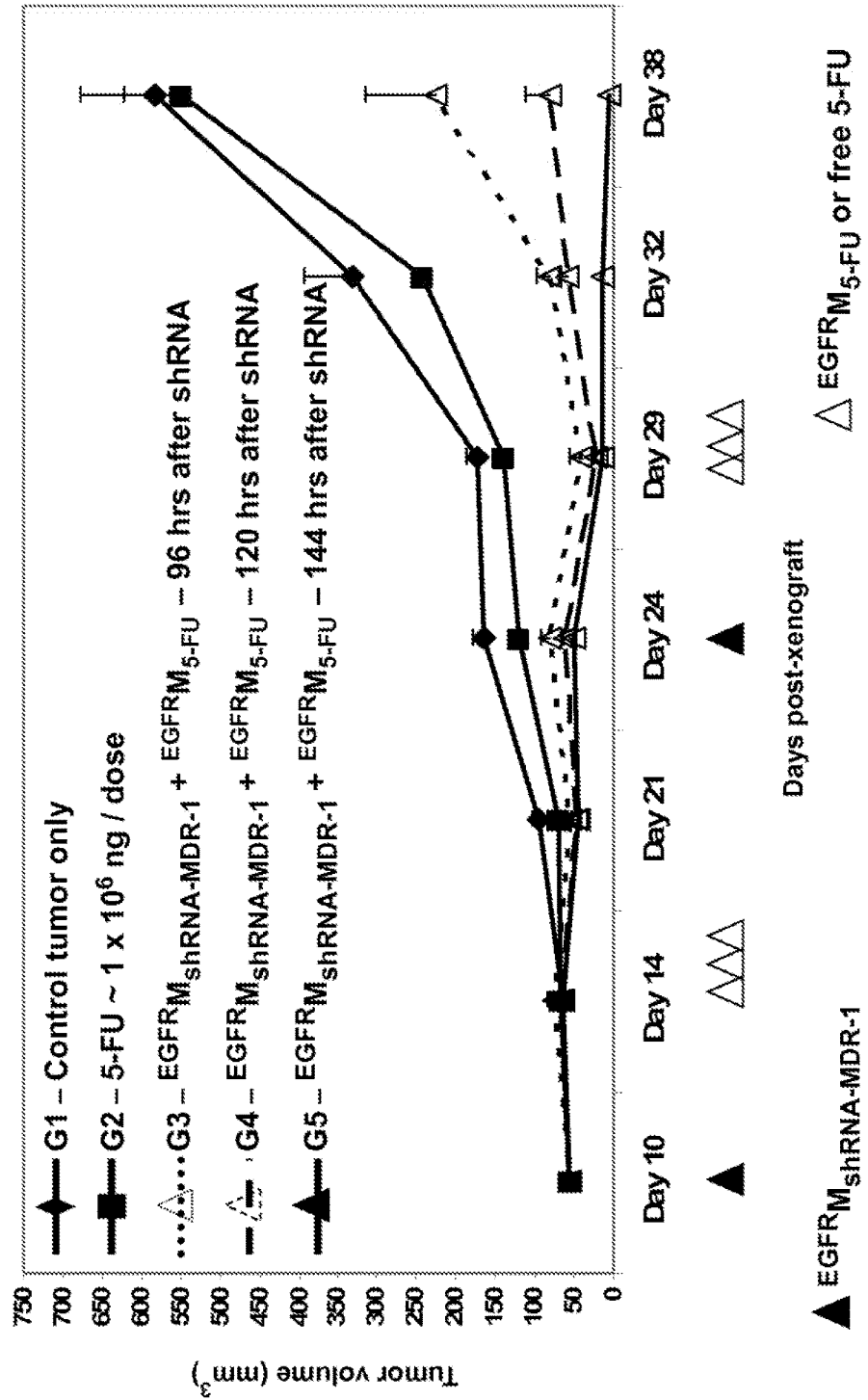
FIG. 6 shows the effect of dosing schedules on reversal of drug-resistance and therapeutic effect. Human colon cancer (Caco-2) xenografts were established in nude mice and the following intravenous treatments were administered: G1—tumor only, G2 (control), free 5-FU, G3 (expt), $^{EGFR}$minicells$_{shRNA-MDR-1}$ followed 96 hrs later by $^{EGFR}$minicells$_{5-FU}$, G4 (expt), $^{EGFR}$minicells$_{shRNA-MDR-1}$ followed 120 hrs later by $^{EGFR}$minicells$_{5-FU}$, and G5 (expt), $^{EGFR}$minicells$_{shRNA-MDR-1}$ followed 144 hrs later by $^{EGFR}$minicells$_{5-FU}$. The bispecific antibody used to target the breast cancer cells carried specificity against S. typhimurium O-antigen on one arm and human EGFR on the other arm. Tumor volume is shown on the y-axis. SEM is shown for each measurement.

The results showed (FIG. 6) that administration of $^{EGFR}$minicells$_{5-FU}$ at 144 hrs after the administration of $^{EGFR}$minicells$_{shRNA-MDR-1}$ (G5) resulted in maximal efficacy of reversal of drug resistance and therapeutic efficacy. The potency of the invention is evident from the concentration of drug required to effectively treat these highly resistant tumors since the minicells carried 3,000-fold and 12,500-fold less drug compared to free irinotecan and 5-FU treatments respectively. The free drugs had no effect on tumor growth as seen in FIGS. 5 and 6.

REFERENCES

All publications and patents mentioned in this specification are incorporated herein by reference. Reference to a publication or patent, however, does not constitute an admission as to prior art.

Ambudkar, et al., Annu. Rev. Pharmacol. Toxicol. 39: 361 (1999).
Antoku, et al., Biochem. Biophys. Res. Commun., 286: 1003 (2001).
Ayesh et al., Anticancer Drugs, 7(6): 678-86 (1996)
Ayesh et al., Biochim. Biophys. Acta, 1316(1): 8-18 (1996)
Bakhshi, et al., Cell, 41: 899 (1985).
Bargou, et al., Int. J. Cancer, 60: 854 (1995).
Batra et al., Gene Ther. 1(4): 255-60 (1994).
Becker et al., Cancer Biol Ther., 1(5):548-53 (2002).
Bredel, Brain Res. Rev., 35: 161 (2001).
Britton et al., Genes Dev., 12: 1254 (1998).
Broxterman et al., Cancer Lett., 35(1): 87-95 (1987).
Brummelkamp, et al., Science 296:550 (2002).
Caplen, Expert Opin. Biol. Ther., 3(4): 575-86 (2003).
Caplen and Mousses, Ann. N.Y. Acad. Sci., 1002: 56-62 (2003).
Carter, P. Nat Rev Cancer, 1(2): 118-29 (2001).
Chen, et al., Int. J. Cancer, 93: 107 (2001).
Ciliberto et al., Cell. 41: 531 (1985).
Cole et al., Science 258:1650-1654 (1992).
Collins & Olive, 32 Biochem. 2795-99 (1993).
Cory et al., Cancer Commun. 3: 207-212 (1991).
Cory, S. Annu. Rev. Immunol., 13: 513-543 (1995).
de Boer et al., J. Bacteriol. 174: 63 (1992).
de Haard, H. J. et al. J. Biol. Chem. 274, 18218-18230 (1999).
Doige et al., Ann. Rev. Microbiol., 47: 291-319 (1993).

Dubel et al., J. Immunol. Methods, 178: 201-209 (1995).
Duan et al., Mol. Cancer Therapeutics, 3(7): 833-38 (2004).
Duxbury et al., J. Am. Coll. Surg., 198: 953-59 (2004).
Elbashir et al., Genes Dev., 15(2):188-200 (2001).
Elbashir et al., Nature, 411(6836):494-8 (2001).
Endicott et al., Ann. Rev. Biochem., 58: 137-71 (1989).
Fardel et al., Gen Pharmacol., 27(8):1283-1291 (1996).
Forbes, Australian J. Biotechnology 1: 30 (1987).
Frain et al., Mol. Cell Biol., 10: 991 (1990).
Frankel et al., Leukemia, 14: 576-585 (2000).
Gariboldi et al., Int. J. Oncology, 22: 1057-64 (2003).
Glennie et al., J. Immunol., 139(7):2367-75 (1987).
Gosselin et al., Biotechnol. Annu. Rev., 8:103-31 (2002).
Gottesman, et al., Nat. Rev. Cancer 2: 48 (2002).
Griffiths et al., EMBO J. 13: 3245-3260 (1994).
Guerrier-Takada et al., Cell, 35: 849 (1983).
Hampel and Tritz, Biochem., 28: 4929 (1989).
Hampel et al., Nucleic Acids Research: 299 (1990)
Hanada, et al., J. Biol. Chem., 270: 11962 (1995).
Hanahan, Nature, 315: 115 (1985).
Hannon, Nature (Lond.), 418: 244 (2002).
Harry, Mol. Microbiol., 40: 795 (2001).
Hart, Semin. Oncol., 23: 154 (1996).
Heim et al., Proc. Nat'l. Acad. Sci. USA, 91: 12501 (1994).
Hiraga et al., J. Bacteriol., 171: 1496 (1989).
Hoshida et al., Pancreas, 25(2):111-21 (2002).
Hu et al., Cancer Res., 56: 3055-3061 (1996).
Hu et al., Mol. Microbiol., 34:82-90 (1999).
Hunter et al., Mol. Cell. Biol., 16: 877 (1996).
Hudson & Souriau, Expert Opin. Biol. Ther. 1: 845-855 (2001).
Hudson & Souriau, Nat. Med., 9 (1):129-34 (2003).
Hung et al., Adv. Exp. Med. Biol., 465:171-80 (2000).
Hutvagner & Zamore, Curr. Opin. Genet. Dev., 12: 225 (2002).
Ireton et al., J. Bacteriol. 176: 5320 (1994).
Jones et al., Nature 321: 522-525 (1986).
Juliano & Ling, Biochimica et Biophysica Acta, 455:152 (1976).
Kaetzel et al., Biochem. Soc. Trans. 25:475-480 (1997).
Karpovsky et al., J. Exp. Med., 160(6):1686-701 (1984).
Katabi et al., Human Gene Therapy 10: 155 (1999).
Kelsey et al., Genes and Devel. 1: 161 (1987).
Kleeff et al., Cancer Gene Ther., 9(6):522-32 (2002).
Knappik et al., J. Mol. Biol. 296: 57-86 (2000).
Kostelny et al., J. Immunol. 148(5):1547-53 (1992).
Kroemer, Nat. Med., 3: 614 (1997).
Kurane et al., Jpn. J. Cancer Res. 89: 1212 (1998).
Leder et al., Cell 45: 485 (1986).
Lehnert, Eur. J. Cancer, A(6): 912-20 (1996).
Levin et al., J. Bacteriol. 174: 6717 (1992).
List, Oncology, 7(10): 23-8, 32, 35-38 (1993).
List et al., J. Clin. Oncol., 11(9): 1652-60 (1993).
Litman, et al., J. Cell Sci., 113: 2011 (2000).
Litman et al., Cell Mol. Life Sci., 58(7): 931-59 (2001).
MacDonald et al., Hepatology 7: 425 (1987).
Mason et al., Science 234: 1372 (1986).
McCubrey, et al., Cell Cycle Checkpoints and Cancer, pp. 17-53. Georgetown, Tex.: Landes Bioscience, (2001a).
McCubrey, et al., Leukemia, 15: 1203 (2001).
Miller et al., J. Clin. Oncol., 9(1): 17-24 (1991).
Morton & Potter, J. Pharmacology & Exper. Therapeutics 286: 1066 (1998).
Nieth et al., FEBS Letters, 545: 144-50 (2003).
Nyati et al., Clin Cancer Res. 10; 691-700 (2004).
Okada et al., Sci. Prog. 77: 253 (1993-94).
Okada et al., J. Bacteriol. 176: 917 (1994).

Osbourn et al., Drug Delivery Tech., 8: 845-851 (2003).
Pack et al., Biochemistry, 31(6):1579-84 (1992).
Perrotta and Been, Biochem., 31: 16 (1992)
Pikaar et al., J. Infect. Dis. 172: 481 (1995).
Pinkert et al., Genes and Devel. 1: 268 (1987).
Prasher et al., Trends in Genetics 11: 320 (1995).
Raskin & de Boer, J. Bacteriol. 181: 6419 (1999).
Readhead et al., Cell 48: 703 (1987).
Reeve & Cornett, J. Virol. 15: 1308 (1975).
Ridgway et al., Protein Eng., 9(7): 617-21 (1996).
Riezman, Trends in Cell Biology, 3: 330 (1993).
Rossi et al., Aids Research and Human Retroviruses, 8: 183 (1992)
Salomon et al., Crit. Rev. Oncol. Hematol., 19: 183-232 (1995).
Salveson et al., Cell, 91: 443 (1997).
Sandvig & Deurs, Trends in Cell Biology, 4: 275 (1994).
Sato, et al., Proc. Natl. Acad. Sci. USA, 91: 9238 (1994).
Sattler, et al., Science (Wash. D.C.), 275: 983 (1997).
Saville & Collins, Cell, 61: 685-96 (1990).
Saville & Collins, PNAS (USA), 88: 8826-30 (1991).
Scheffer, et al., Curr. Opin. Oncol., 12: 550 (2000).
Sellers & Fisher, J. Clin. Invest., 104: 1655 (1999).
Sharp, Genes Dev., 15: 485 (2001).
Shaw & Griffen, Nature 289: 409 (1981).
Sheets et al., Proc. Natl Acad. Sci. USA, 95: 6157-6162 (1998).
Siould, "Therapeutic siRNAs," Trends in Pharmacological Sciences, 25(1): 22-28 (2004).
Speert et al., J. Clin. Invest., 82: 872 (1988).
Stewart & D'Ari, J. Bacteriol., 174: 4513 (1992).
Sun, et al., Biochem. Biophys. Res. Commun., 280: 788 (2001).
Swift et al., Cell, 38: 639 (1984).
Thurnher et al., Glycobiology, 4(4):429-35 (1994).
Todorovska et al., J. Immunol. Methods, 248: 47-66 (2001).
Tomlinson & Holliger, Methods Enzymol., 326: 461-479 (2000).
U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,496,778
U.S. Pat. No. 4,987,071
U.S. Pat. No. 4,975,278
U.S. Pat. No. 5,037,743
U.S. Pat. No. 5,143,830
U.S. Pat. No. 5,260,203
U.S. Pat. No. 5,455,030
U.S. Pat. No. 5,530,101
U.S. Pat. No. 5,585,089
U.S. Pat. No. 6,025,197
U.S. Pat. No. 6,639,055
U.S. published patent application No. 2004-0265994
Van Bambeke, et al., Biochem. Pharmacol., 60: 457 (2000).
Vaughan, et al., Nature Biotechnol., 14: 309-314 (1996).
Vaughan et al., Nature Biotechnol., 16: 535-539 (1998).
Wachi et al., J. Bacteriol., 171: 6511 (1989).
Wang, et al., Nat. Med., 5: 412 (1999).
Wang et al., Proc. Natl. Acad. Sci. USA, 93: 7063-7068 (1996).
White & McCubrey, Leukemia, 15: 1011-1021 (2001).
WO 81/01145
WO 88/07378

WO 95/21191
WO 00/67776
WO 05/056749
Wu, et al., Cancer Res., 63: 1515-19 (2003).
Wacheck, et al., *Oligonucleotides,* 13: 393 (2003).
Wright & Jong, Experimental Medi., 163: 1245 (1986).
Yague et al., Gene Therapy, 11: 1170-74 (2004).
Ziady et al., Am. J. Physiol., 273(2 Pt 1):G545-52 (1997).

What is claimed is:

1. A composition comprising:
   (a) a first intact, bacterially derived minicell that contains a a functional nucleic acid molecule or a plasmid comprising a segment that encodes a functional nucleic acid molecule, wherein the functional nucleic acid molecule targets (i) a transcript encoding a protein that contributes to apoptosis resistance in tumor cells or (ii) a transcript encoding a protein that contributes to neoplasticity in tumor cells;
   (b) a second intact, bacterially derived minicell that is separate from the first minicell and that contains a drug; and
   (c) a pharmaceutically acceptable carrier for each of (a) and (b).

2. The composition of claim 1, wherein the drug is selected from chemotherapeutic agents, immunosuppressive agents, cytokines, cytotoxic agents, nucleolytic compounds, radioactive isotopes, receptors, and pro-drug activating enzymes.

3. The composition of claim 1, wherein the functional nucleic acid molecule is an siRNA, shRNA, miRNA, RNAi, antisense, or ribozyme molecule.

4. The composition of claim 1, wherein the plasmid comprises a promoter dependent on RNA polymerase operably linked to the segment that encodes a functional nucleic acid.

5. The composition of claim 1, wherein the functional nucleic acid molecule targets the transcript of a protein that contributes to apoptosis resistance.

6. The composition of claim 1, wherein the functional nucleic acid molecule targets a transcript of Bcl-2, Bcl-$X_L$, A1/Bfl 1, focal adhesion kinase or p53 protein.

7. The composition of claim 1, wherein the functional nucleic acid molecule targets a transcript of a protein that contributes to neoplasticity.

8. The composition of claim 1, wherein the functional nucleic acid molecule targets a transcript of β-Catenin, PKC-α, C-RAF, K-Ras, DP97 Dead box RNA helicase, DNMT1, FLIP, C-Sfc, 53BPI, Polycomb group protein EZH2, ErbB1, HPV-16 E5 and E7, Fortilin & MCI1P, DIP13α, MBD2, p21, KLF4, tpt/TCTP, SPK1 & SPK2, P300, PLK1, Trp53, Ras, ErbB1, VEGF, or BAG-1.

9. The composition of claim 1, wherein the plasmid encodes multiple functional nucleic acid molecules.

10. The composition of claim 9, wherein the plasmid further comprises a promoter for each encoded functional nucleic acid molecule.

11. The composition of claim 1, wherein each minicell further comprises a bispecific ligand.

12. The composition of claim 11, wherein the bispecific ligand comprises a first arm that carries specificity for a minicell surface structure and a second arm that carries specificity for a non-phagocytic mammalian cell surface receptor.

13. The composition of claim 12, wherein the mammalian cell surface receptor is capable of activating receptor-mediated endocytosis of the minicell.

14. The composition of claim 11, wherein the bispecific ligand comprises an antibody or antibody fragment.

15. The composition of claim 1, wherein the composition contains fewer than about 1 contaminating parent bacterial cell per $10^7$ minicells.

16. The composition of claim 1, wherein the composition contains fewer than about 1 contaminating parent bacterial cell per $10^8$ minicells.

17. The composition of claim 1, wherein the composition contains fewer than about 1 contaminating parent bacterial cell per $10^9$ minicells.

18. The composition of claim 1, wherein the composition contains fewer than about 1 contaminating parent bacterial cell per $10^{10}$ minicells.

19. The composition of claim 1, wherein the composition comprises at least one additional intact, bacterially derived minicell, wherein the at least one additional minicell comprises a payload different from the first and second minicells.

* * * * *

SEQUENCE LISTING

<160> NUMBER OF SEQ ID NOS: 2

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgaaagaaa ccaactgtca gtgtagagta ctgtacactg acagttggtt tcttttttt        59

<210> SEQ ID NO 2
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tcgatgtgga tgactgagta cctgagagta ctgtcaggta ctcagtcatc cacattttt        59